(12) United States Patent
Boudreaux

(10) Patent No.: US 11,039,877 B2
(45) Date of Patent: Jun. 22, 2021

(54) LATCHING CLAMP ARM FOR ELECTROSURGICAL SHEARS

(71) Applicant: ETHICON LLC, Guaynabo, PR (US)

(72) Inventor: Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 413 days.

(21) Appl. No.: 15/989,455

(22) Filed: May 25, 2018

(65) Prior Publication Data
US 2019/0357968 A1    Nov. 28, 2019

(51) Int. Cl.
*A61B 18/14* (2006.01)
*A61B 18/12* (2006.01)
*A61B 18/00* (2006.01)

(52) U.S. Cl.
CPC ...... *A61B 18/1442* (2013.01); *A61B 18/1206* (2013.01); *A61B 2018/0063* (2013.01); *A61B 2018/00601* (2013.01); *A61B 2018/126* (2013.01); *A61B 2018/1455* (2013.01)

(58) Field of Classification Search
CPC ............ A61B 18/1206; A61B 18/1442; A61B 17/2833; A61B 2018/00601; A61B 2018/0063; A61B 2018/126; A61B 2018/1455
See application file for complete search history.

(56) References Cited

U.S. PATENT DOCUMENTS

| | | |
|---|---|---|
| 6,500,176 B1 | 12/2002 | Truckai et al. |
| 6,511,480 B1 * | 1/2003 | Tetzlaff .............. A61B 18/1445 606/51 |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,232,440 B2 * | 6/2007 | Dumbauld ......... A61B 18/1445 606/51 |
| 7,309,849 B2 | 12/2007 | Truckai et al. |

(Continued)

OTHER PUBLICATIONS

International Search Report and Written Opinion dated Sep. 18, 2019 for International Application No. PCT/IB2019/053686, 16 pages.

(Continued)

*Primary Examiner* — Michael F Peffley
(74) *Attorney, Agent, or Firm* — Frost Brown Todd LLC

(57) ABSTRACT

A surgical instrument includes an end effector, a handle assembly, and a latch assembly. The end effector includes a first jaw, a second jaw pivotably coupled with the first jaw, a knife, and an electrode assembly. The handle assembly includes a housing associated with the first jaw, and an arm associated with the second jaw. The arm can pivot the second jaw between an open position and a closed position. The latch assembly can transition between an unlatched configuration and a latched configuration. The latch assembly can prevent the arm from pivoting the second jaw from the closed position toward the open position in the latched configuration. The latch assembly can allow the arm to pivot the second jaw from the closed position toward the open position in the unlatched configuration.

18 Claims, 23 Drawing Sheets

(56) References Cited

U.S. PATENT DOCUMENTS

| | | | |
|---|---|---|---|
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 7,628,791 | B2 * | 12/2009 | Garrison ............ A61B 18/1445 606/51 |
| 7,909,823 | B2 * | 3/2011 | Moses ................ A61B 17/3201 606/51 |
| 8,939,974 | B2 | 1/2015 | Boudreaux et al. |
| 9,089,327 | B2 | 7/2015 | Worrell et al. |
| 9,161,803 | B2 | 10/2015 | Yates et al. |
| 9,402,682 | B2 | 8/2016 | Worrell et al. |
| 9,545,253 | B2 | 1/2017 | Worrell et al. |
| 9,610,114 | B2 | 4/2017 | Baxter, III et al. |
| 9,877,720 | B2 | 1/2018 | Worrell et al. |
| 2014/0031821 | A1 | 1/2014 | Garrison |
| 2016/0051273 | A1 | 2/2016 | Batchelor et al. |
| 2016/0175030 | A1 * | 6/2016 | Boudreaux ........ A61B 18/1442 606/42 |
| 2016/0175031 | A1 * | 6/2016 | Boudreaux ........ A61B 18/1442 606/52 |
| 2017/0281211 | A1 * | 10/2017 | Strobl ................ A61B 18/1445 |

OTHER PUBLICATIONS

U.S. Appl. No. 15/989,424, entitled "Method and Apparatus for Open Electrosurgical Shears," filed May 25, 2018.

U.S. Appl. No. 15/989,430, entitled "Electrosurgical Shears with Knife Lock and Clamp-Actuated Switch," filed May 25, 2018.

U.S. Appl. No. 15/989,433, entitled "Knife Drive Assembly for Electrosurgical Shears," filed May 25, 2018.

U.S. Appl. No. 15/989,438, entitled "Knife Auto-Return Assembly for Electrosurgical Shears," filed May 25, 2018.

U.S. Appl. No. 15/989,442, entitled "Compound Screw Knife Drive for Electrosurgical Shears," filed May 25, 2018.

U.S. Appl. No. 15/989,448, entitled "Firing and Lockout Assembly for Knife for Electrosurgical Shears," filed May 25, 2018.

U.S. Appl. No. 15/989,452, entitled "Dual Stage Energy Activation for Electrosurgical Shears," filed May 25, 2018.

\* cited by examiner

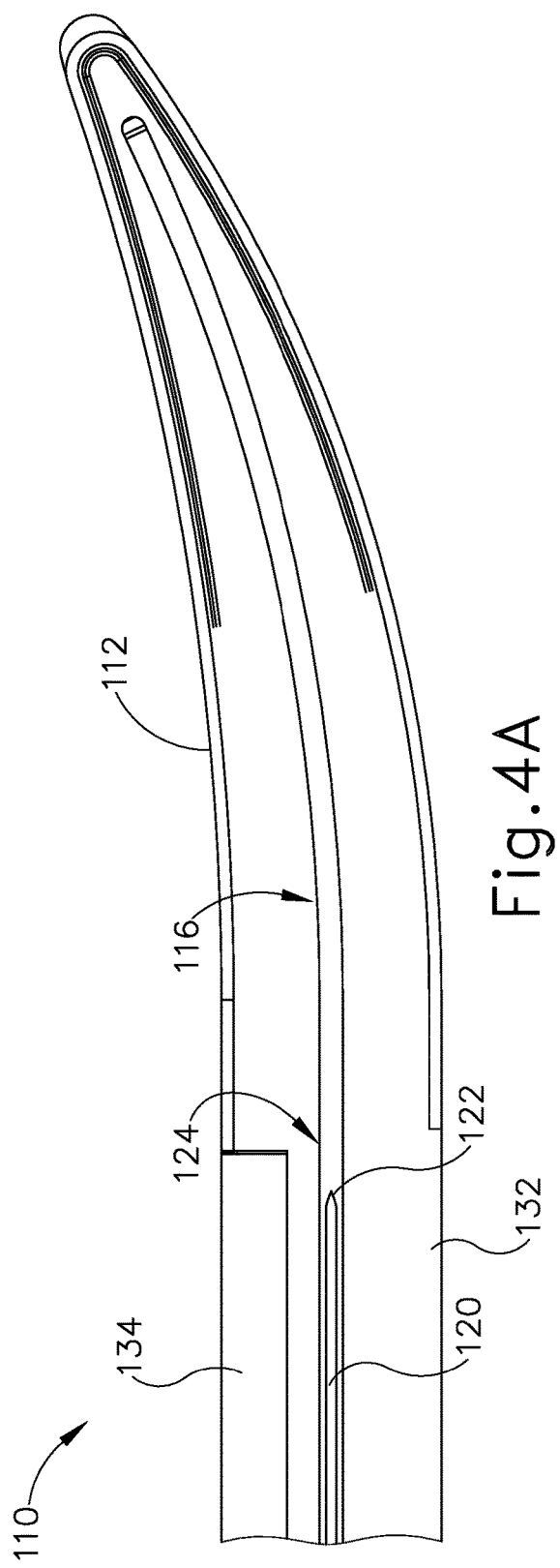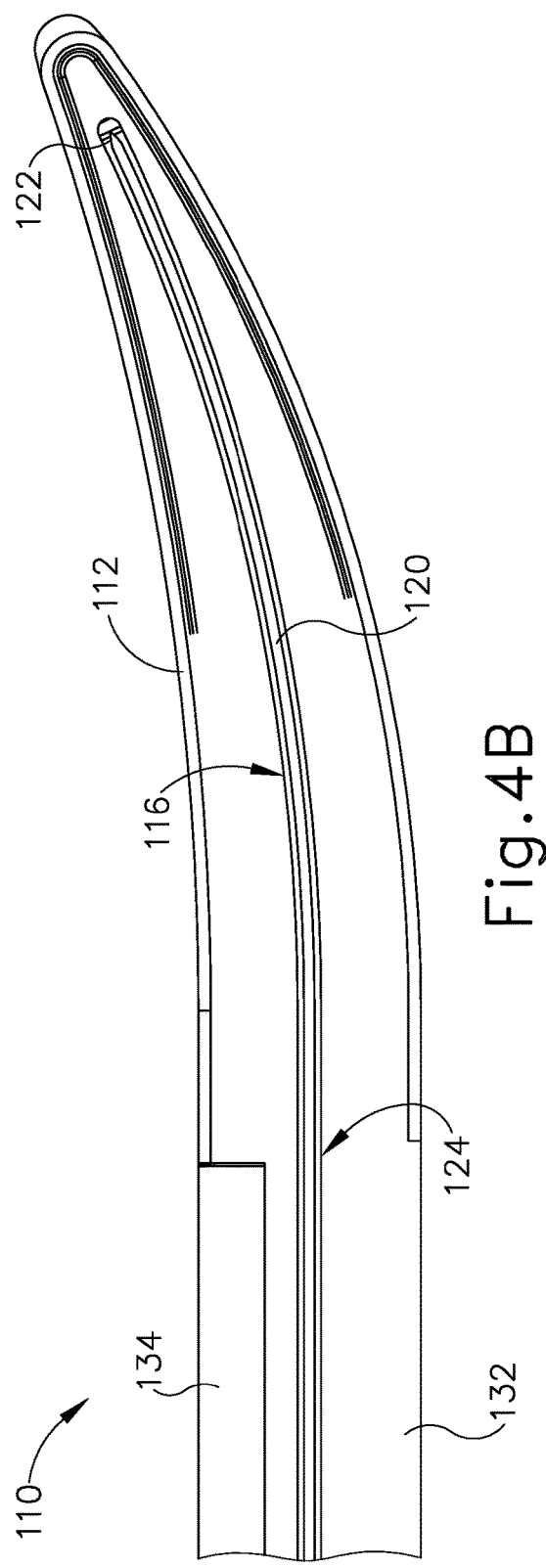

LATCHING CLAMP ARM FOR ELECTROSURGICAL SHEARS

BACKGROUND

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pat. No. 9,877,720, entitled "Control Features for Articulating Surgical Device," issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; and U.S. Pat. No. 9,545,253, entitled "Surgical Instrument with Contained Dual Helix Actuator Assembly," issued Jan. 17, 2017, the disclosure of which is incorporated by reference herein.

Some versions of electrosurgical instruments that are operable to sever tissue may be selectively used in at least two modes. One such mode may include both severing tissue and coagulating tissue. Another such mode may include just coagulating tissue without also severing the tissue. Yet another mode may include the use of jaws to grasp and manipulate tissue without also coagulating and/or severing the tissue. When an instrument includes grasping jaws and tissue severing capabilities, the instrument may also include a feature that ensures full closure of the jaws before the tissue is severed and/or before the electrodes are activated.

While various kinds of surgical instrument have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a cross-sectional view of the end effector of FIG. 1, taken along line 4-4 of FIG. 1, where the translating knife of FIG. 2 is in the proximal position;

FIG. 4B depicts a cross-sectional view of the end effector of FIG. 1, taken along line 4-4 of FIG. 1, where the translating knife of FIG. 2 is in the distal position;

DETAILED DESCRIPTION

Figure 1:
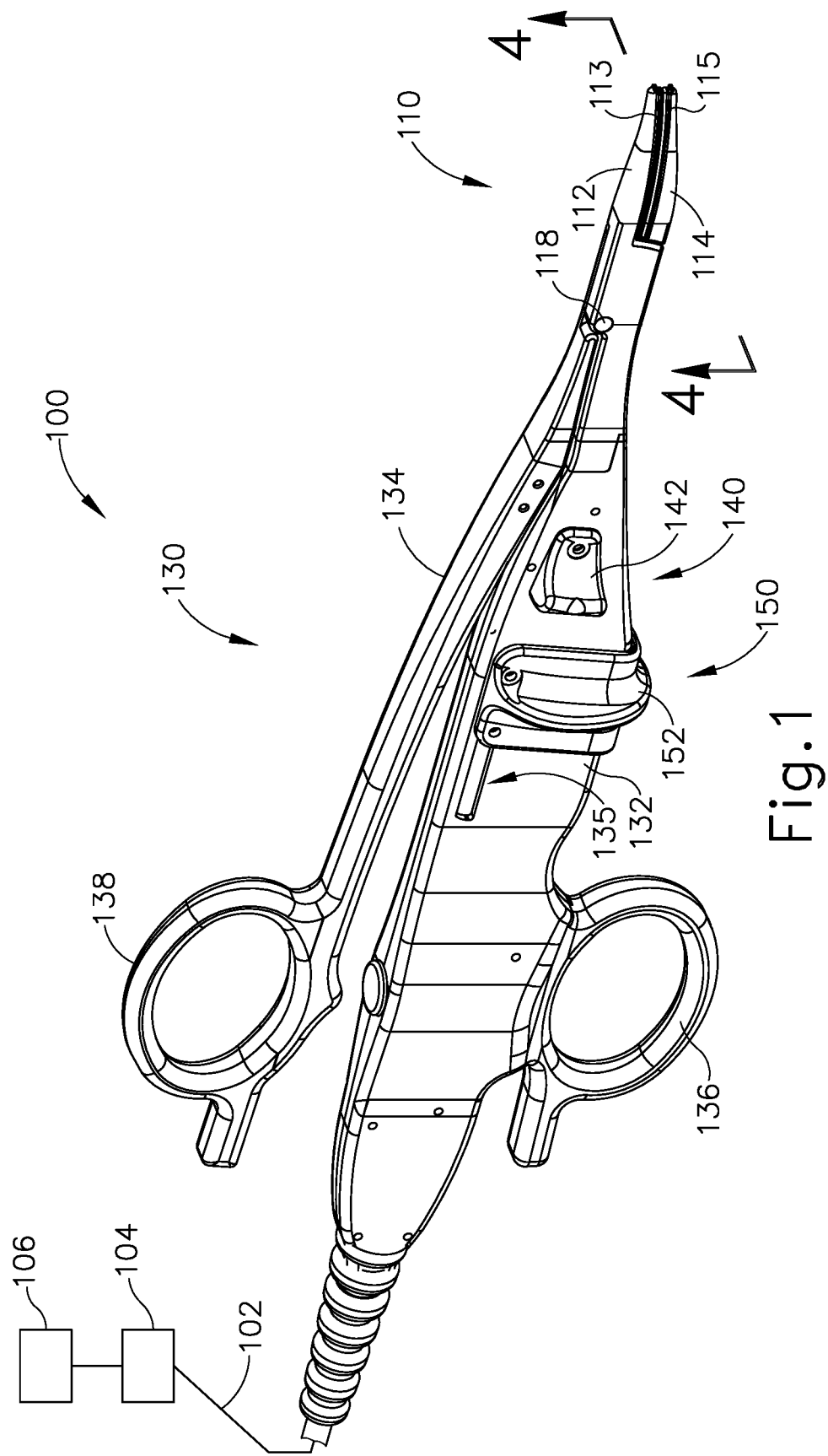
FIG. 1 depicts a perspective view of an exemplary electrosurgical forceps instrument, where an end effector is in a closed position, where a resilient arm is in a relaxed position.
Figure 2:
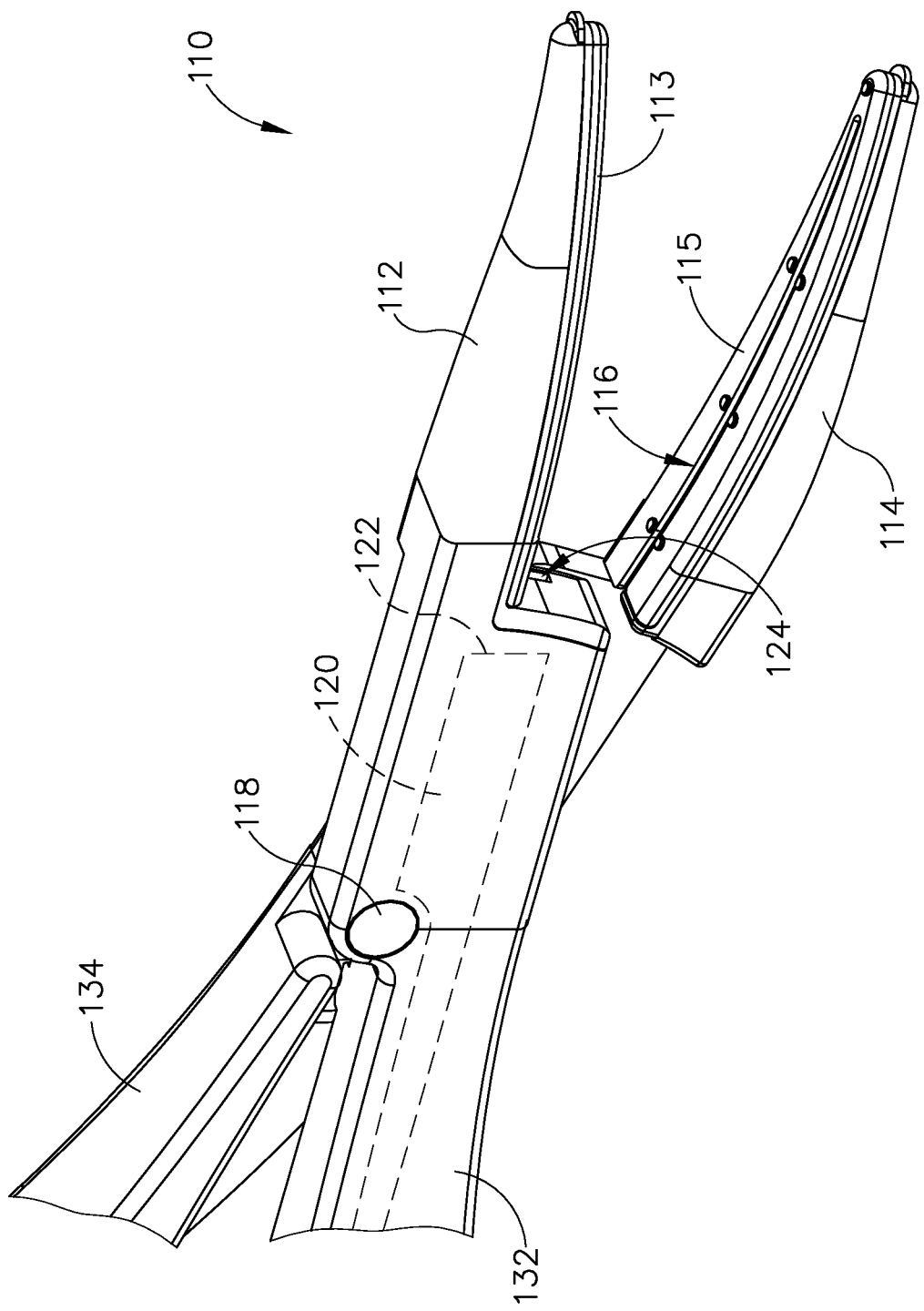
FIG. 2 depicts a perspective view of the end effector of FIG. 1 in an opened position, where a translating knife is in a proximal position.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Electrosurgical Forceps

As previously noted, an electrosurgical instrument may include a set of jaws, with at least one of the jaws being pivotable relative to the other jaw to selectively compress tissue between the jaws. Once the tissue is compressed, electrodes in the jaws may be activated with bipolar RF energy to seal the tissue. In some instances, a cutting feature is operable to sever tissue that is clamped between the jaws. For instance, the cutting feature may be actuated before or after the RF energy has sealed the tissue. Various references that are cited herein relate to electrosurgical instruments where the jaws are part of an end effector at the distal end of an elongate shaft, such that the end effector and the shaft may be inserted through a port (e.g., a trocar) to reach a site within a patient during a minimally invasive endoscopic surgical procedure. A handle assembly may be positioned at the proximal end of the shaft for manipulating the end effector. Such a handle assembly may have a pistol grip configuration or some other configuration.

In some instances, it may be desirable to provide an electrosurgical instrument that does not have an elongate shaft or handle assembly similar to those described in the various references cited herein. In particular, it may be desirable to provide an electrosurgical instrument that is configured similar to a forceps device, with a scissor grip. Such instruments may be used in a variety of medical procedures. Various examples of electrosurgical shears/forceps devices are disclosed in U.S. Pat. No. 9,610,144, entitled "Electrosurgical Hand Shears," filed Jan. 29, 2013, the disclosure of which is incorporated by reference herein. Various other examples of electrosurgical forceps instruments will be described in greater detail below; while other examples will be apparent to those of ordinary skill in the art in view of the teachings herein.

FIGS. 1-4B show an exemplary electrosurgical forceps instrument (100).

Instrument (100) includes a handle assembly (130) extending distally into an end effector (110). As will be described in greater detail below, instrument (100) may be used to grasp, seal, and sever tissue captured by end effector (110).

End effector (110) includes a first jaw (112) having a first electrode (113), a second jaw (114) having a second electrode (115), and a knife (120) configured to translate through the first jaw (112) and the second jaw (114). First jaw (112) and second jaw (114) are pivotably coupled with each other via pivot pin (118). First jaw (112) and second jaw (114) may pivot between an open position (FIG. 2) and a closed position (FIG. 1) in order to grasp tissue. First and second electrodes (113, 115) are positioned on respective jaws (112, 114) such that electrodes (113, 115) face each other when jaws (112, 114) are pivoted into the closed position. Additionally, each electrode (113, 115) is U-shaped in the present example, with the bend of the U-shape located near the distal end of each respective jaw (112, 114), such that each electrode (113, 115) includes two longitudinally extending, laterally spaced-apart legs extending along the length of each respective jaw (112, 114). Laterally spaced-apart legs of each electrode (113, 115) and corresponding portions of jaws (112, 114) define an elongate slot (116). Elongate slot (116) is dimensioned to slidably receive knife (120) such that knife may translate from a proximal position (FIG. 4A) to a distal position (FIG. 4B). Knife (120) includes a distal cutting edge (122) configured to sever tissue captured between jaws (112, 114) in the closed position.

A cable (102) extends proximally from handle assembly (130). Cable (102) is coupled with a control unit (104), which is further coupled with a power source (106). Power source (106) may power control unit (104). Control unit (104) is operable to provide RF power to electrodes (113, 115) of jaws (112, 114), to thereby seal tissue suitably captured between jaws (112, 114).

Handle assembly (130) includes a housing (132), and a resilient arm (134).

Housing (132) contains an electrode activation assembly (140) and a firing assembly (150). Housing (132) and resilient arm (134) are pivotably coupled with each other via pivot pin (118). Housing (132) extends distally into first jaw (112), while resilient arm (134) extends distally into second jaw (114). Housing (132) defines a knife pathway (124) that slidably houses knife (120). Housing (132) includes a finger ring (136) while resilient arm (134) terminates proximally into a thumb ring (138). Therefore, the operator may grasp instrument (100) in a scissor grip fashion and pivot resilient arm (134) relative to housing (132) via rings (136, 138) in order to open and close jaws (112, 114).

Resilient arm (134) is sufficiently resilient that arm (134) may flex from a relaxed position (FIG. 3B) to a flexed position (FIG. 3C) in response to pivoting arm (134) further toward housing (132) when jaws (112, 114) are already in the closed position. Resilient arm (134) is biased toward the relaxed position. Further pivoting of resilient arm (134) into the flexed position may result in greater closure forces between jaws (112, 114) as compared to pivoting jaws (112, 114) into the closed position while arm (134) is in the relaxed position. Resilient arm (134) may be suitably resilient such that when resilient arm (134) is pivoted into the flexed position, the closure force between jaws (112, 114) is sufficient such that electrodes (113, 115) may properly seal tissue grasped between jaws (112, 114). Additionally, the resilient nature of arm may limit the amount of closure force between jaws (112, 114) such that jaws (112, 114) may not compress tissue too much, resulting in inadvertent tissue damage. When the operator no longer desires to compress tissue between jaws (112, 114) to properly seal clamped tissue, the operator may reduce the amount of closure force applied to resilient arm (134) such that arm (134) returns to the relaxed state.

Housing (132) slidingly supports an RF trigger (142) of electrode activation assembly (140). RF trigger (142) is in communication with control unit (104). RF trigger (142) may be pressed or actuated to command control unit (104) to supply RF energy to electrodes (113, 115) of end effector (110). RF trigger (142) may electrically couple with control unit (104) through any suitable components known to a person having ordinary skill in the art in view of the teachings herein.

As will be described in greater detail below, firing assembly (150) is configured to actuate knife (120) within jaws (112, 114) from a proximal position to a distal position in order to sever tissue captured between jaws (112, 114). Previous firing assemblies for electrosurgical forceps may have had a trigger that was a lever arm configured to rotate relative to a handle assembly to actuate a knife. The lever arm may have extended away from the handle assembly in order to provide a mechanical advantage for actuating knife within jaws (112, 114). However, when lever arm extends away from handle assembly, it may become difficult rotate lever arm when instrument is flipped such that thumb ring becomes finger rings and vice versa. In such instances when instrument is flipped, the lever arm may no longer associate with the index/middle finger for actuating the lever arm.

Therefore, it may be desirable to have a compact firing assembly with a trigger close to the center of housing such that it is easy to actuate firing assembly with the same finger(s), even when instrument is flipped. Firing assembly (150) of the current example includes a knife trigger (152) slidably coupled with housing (132) via a slot (135). Trigger (152) is close to the center of housing (132) such that trigger (152) may be easily accessed regardless if instrument (100) is flipped around. Trigger (152) may actuate relative to housing (132) in order to actuate a knife (120) of end effector (110). In particular, proximal translation of trigger (152) results in distal translation of knife (120), while distal translation of trigger (152) results in proximal translation of knife (120). Trigger (152) may be biased toward the distal position such that knife (120) is biased toward the proximal position.

Trigger (152) may be coupled with knife (120) through any suitably firing mechanism assembly as would be apparent to one having ordinary skill in the art in view of the teachings herein. It should be understood that trigger (152) may be selectively actuated at any suitable time the operator desires. For instance, the operator may grasp tissue by pivoting jaws (112, 114) to the closed position, wait a desired amount of time, and fire trigger (152) to actuate knife (120) and sever tissue. Alternative, the operator may grasp tissue by pivoting jaws (112, 114), release tissue if jaws (112, 114) are not satisfactorily grasping tissue, re-grasp tissue, and then fire trigger (152) to actuate knife (120) and sever tissue.

Figure 3A:
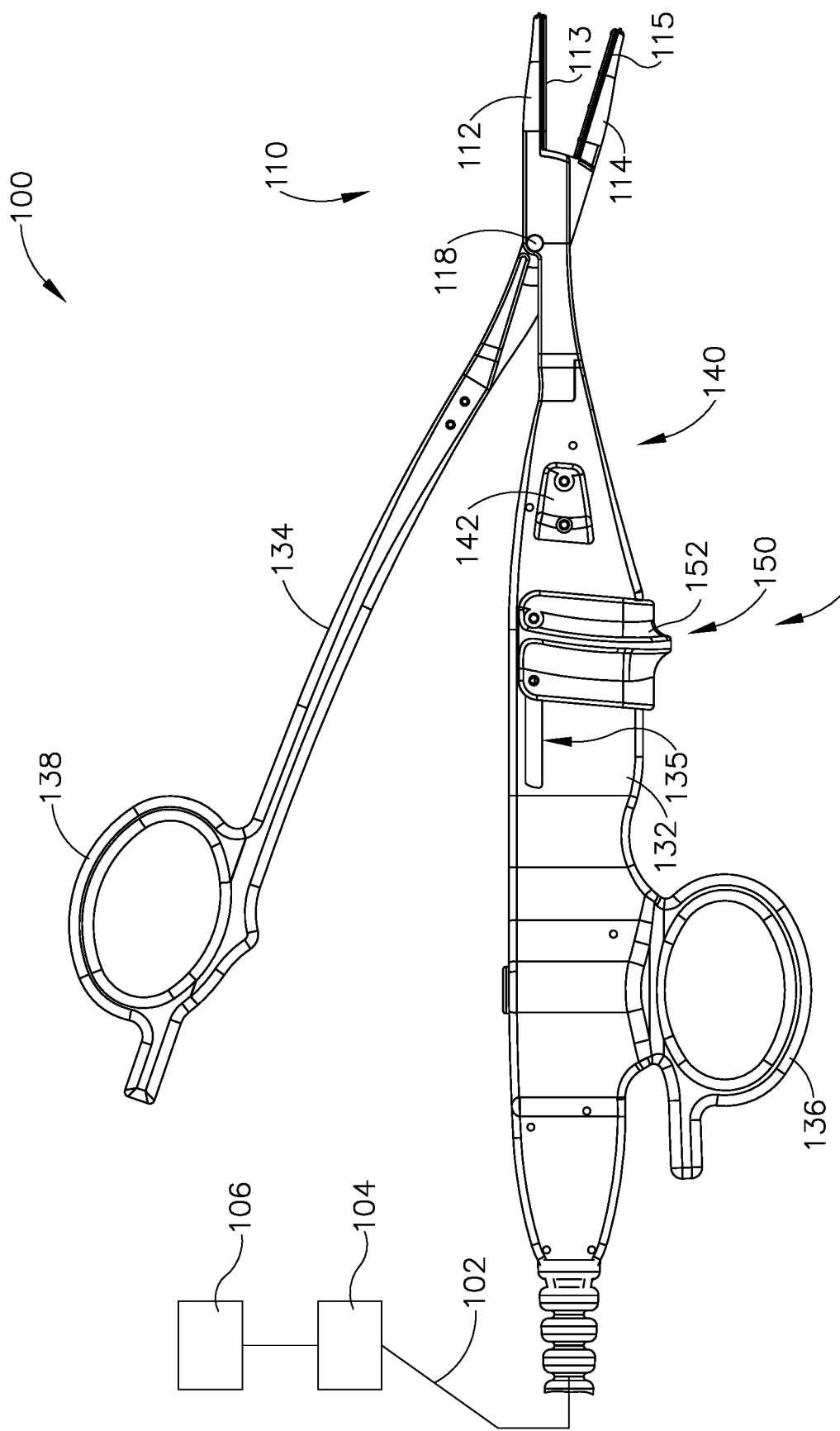
FIG. 3A depicts a side elevational view of the electrosurgical forceps instrument of FIG. 1, where the end effector is in the opened position, where the resilient arm is in the relaxed position, and where the translating knife of FIG. 2 is in the proximal position.

FIGS. 3A-4B show an exemplary operation of instrument (100). FIG. 3A shows jaws (112, 114) of end effector (110) in the opened position. Therefore, resilient arm (134) is pivoted away from housing (132). As shown in FIG. 3B, when the operator desires to initially grasp and manipulate tissue, the operator may pivot resilient arm (134) toward housing (132) such that jaws (112, 114) are pivoted toward the closed position while resilient arm (134) remains in the relaxed position. With jaws (112, 114) pivoted toward the closed position, the operator may manipulate tissue grasped by jaws (112, 114). It should be understood that the closure forces imparted on tissue by jaws (112, 114) at this point may not be sufficient enough for suitable sealing of tissue via RF energy provided by electrodes (113, 115).

Figure 3B:
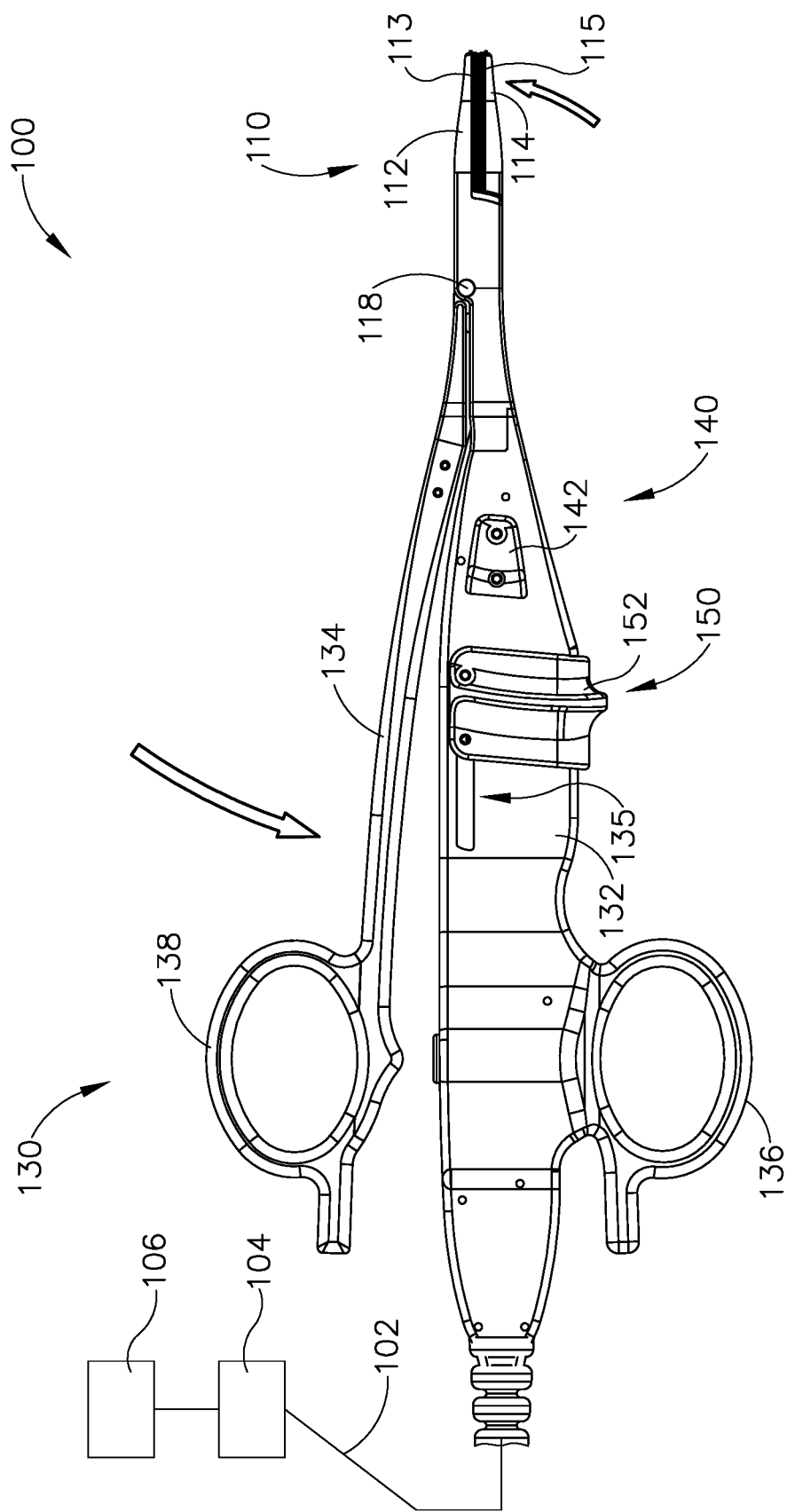
FIG. 3B depicts a side elevational view of the electrosurgical forceps instrument of FIG. 1, where the end effector is in the closed position, where the resilient arm is in the relaxed position, and where the translating knife of FIG. 2 is in the proximal position.
Figure 3C:
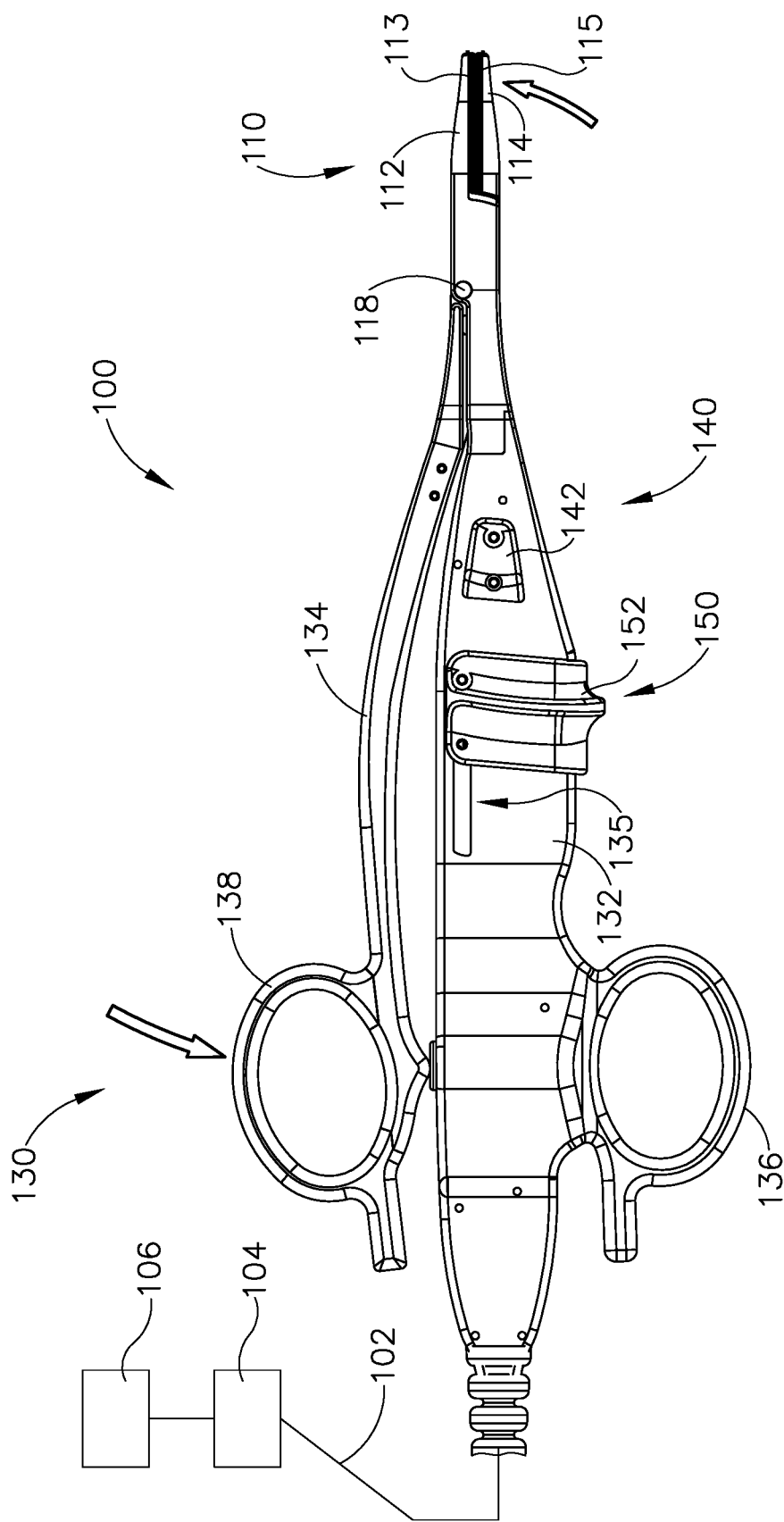
FIG. 3C depicts a side elevational view of the electrosurgical forceps instrument of FIG. 1, where the end effector is in the closed position, where the resilient arm is in a flexed position, and where the translating knife of FIG. 2 is in the proximal position.
Figure 3D:
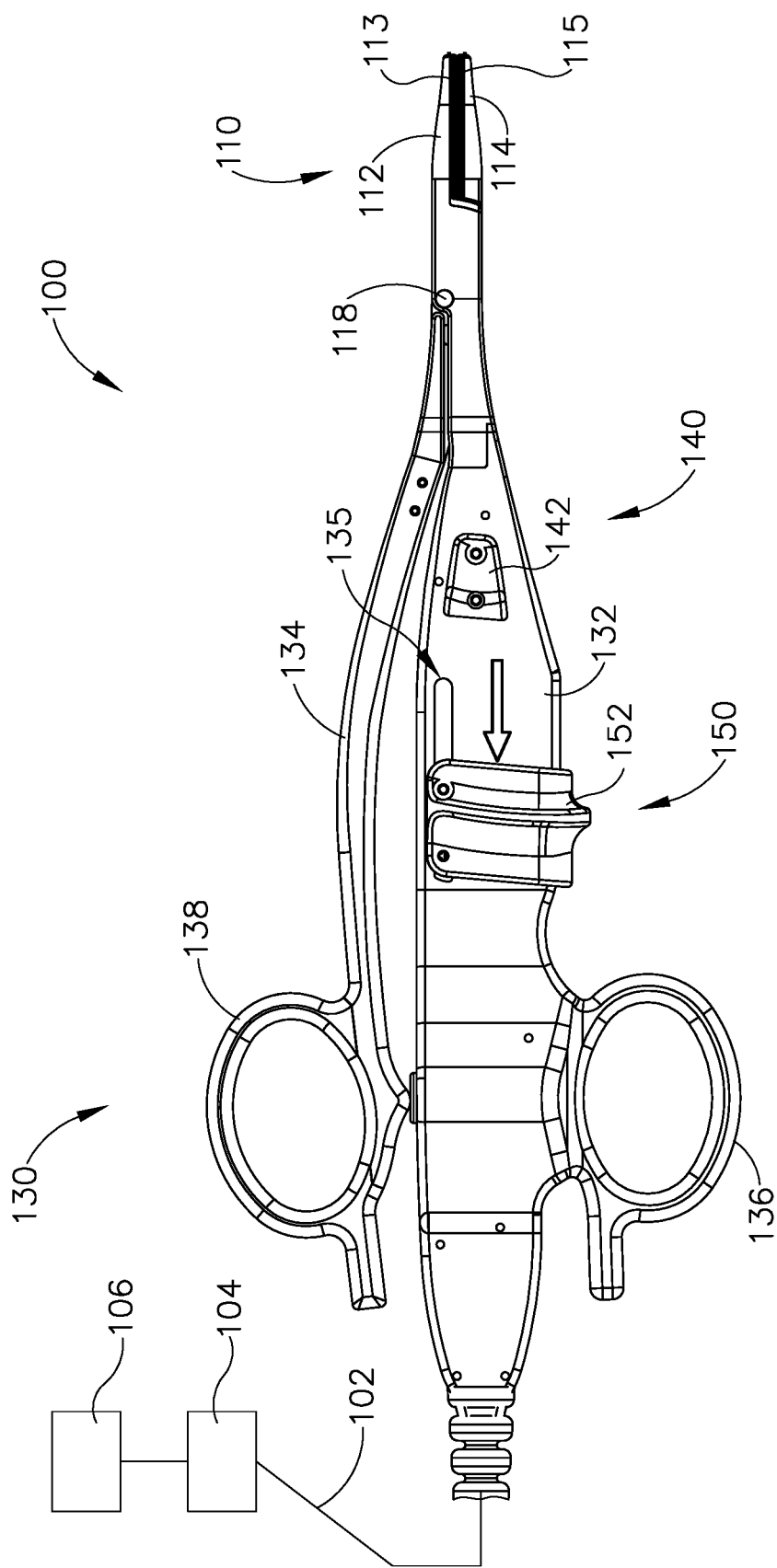
FIG. 3D depicts a side elevational view of the electrosurgical forceps instrument of FIG. 1, where the end effector is in the closed position, where the resilient arm is in the flexed position, and where the translating knife of FIG. 2 is in a distal position.

Next, as shown in FIG. 3C, if the operator desires to apply RF energy to grasped tissue, the operator may further pivot resilient arm (134) toward housing (132) such that resilient arm bends to the flexed position. As this point, the closure forces imparted on tissue by jaws (112, 114) is sufficient for proper sealing. The operator may then actuate RF trigger (142) such that electrodes (113, 115) provide RF energy to grasped tissue. Next, as shown between FIGS. 3C-3D and 4A-4B, the operator may desire to sever tissue captured between jaws (112, 114). Therefore, the operator may actuate trigger (152) proximally as shown between FIGS. 3C-3D such that knife (120) actuates distally as shown between FIGS. 4A-4B. Cutting edge (122) may sever tissue captures between jaws (112, 114) as knife (120) actuates distally through elongate slot (116).

While in the current example, the operator applies RF energy to grasped tissue and then subsequently severs the tissue, the operator may alternatively sever grasped tissue first, then apply RF energy to the tissue as would be apparent to one of ordinary skill in the art in accordance with the teachings herein. Alternatively, the operator may only seal grasped tissue by applying RF energy, without severing the tissue, as would be apparent to one of ordinary skill in the art in accordance with the teachings herein. Alternately, the operator may only sever grasped tissue, without sealing the tissue, as would be apparent to one of ordinary skill in the art in accordance with the teachings herein. Alternatively, the operator may just grasp tissue, without severing or sealing the tissue, as would be apparent to one of ordinary skill in the art in accordance with the teachings herein.

II. Alternative Exemplary Electrosurgical Forceps with Two-Stage Energy Activation As mentioned above, resilient arm (134) may flex toward housing (132) when jaws (112, 114) are in the closed position to provide greater closure forces between jaws (112, 114). The closure forces provided by flexing resilient arm (134) may help activated electrodes (113, 115) properly seal tissue grasped between jaws (112, 114). During exemplary use, if the operator fails to generate enough closure force while jaws (112, 114) are in the closed position, electrodes (113, 115) may fail to properly seal tissue grasped between jaws (112, 114). After long periods of keeping resilient arm (134) in the flexed position, the operator may be come fatigued. Therefore, it may be desirable to provide a latching assembly configured to selectively latch resilient arm (134) in the flexed position such that the operator may choose when the latching assembly holds resilient arm (134) in the flexed position and when the latching assembly releases resilient arm (134) toward the relaxed position. Additionally, it may be desirable to provide a mechanism that indicates when jaws (112, 114) provide a suitable closure force for sealing grasped tissue or prevents electrodes (113, 115) from activating unless jaws (112, 114) provide a suitable closure force for sealing grasped tissue.

In some instances, the operator may accidentally actuate knife trigger (152) proximally while jaws (112, 114) are open, inadvertently exposing distal cutting edge (122) of knife (120) within slot (116). Therefore, it may be desirable to provide a mechanism that prevents actuation of knife until jaws (112, 114) are sufficiently closed.

While various examples of RF activation assemblies are described below, it should be understood various combinations or modifications may be made to such RF activation assemblies as would be apparent to one having ordinary skill in the art in view of the teachings herein.

Figure 5:
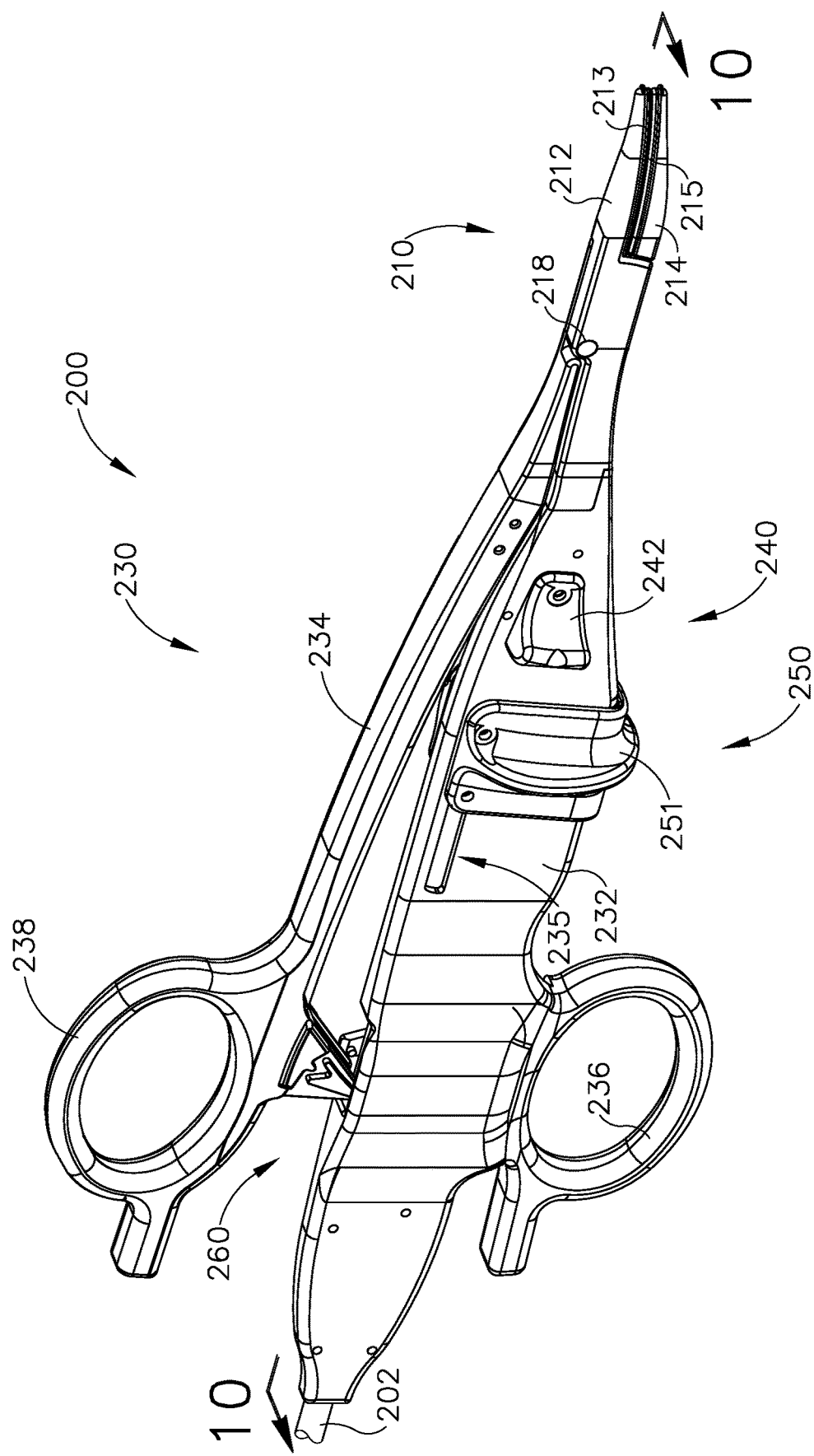
FIG. 5 depicts a perspective view of another exemplary electrosurgical forceps instrument, where an end effector is in a closed position, and where a resilient arm is in a relaxed position.

FIG. 5 shows an alternative exemplary electrosurgical forceps instrument (200) that may be used in replacement of instrument (100) described above. Therefore, as will be described in greater detail below, instrument (200) may be used to grasp, seal, and sever tissue. Instrument (200) includes an end effector (210), a handle assembly (230), an electrode activation assembly (240), a firing assembly (250), and a latching assembly (260). End effector (210) is substantially similar to end effector (110) described above, with differences elaborated below. End effector (210) includes a first jaw (212) having a first electrode (213), a second jaw (214) having a second electrode (215), and a knife (220) configured to translate through the first jaw (212) and the second jaw (214).

Figure 6:
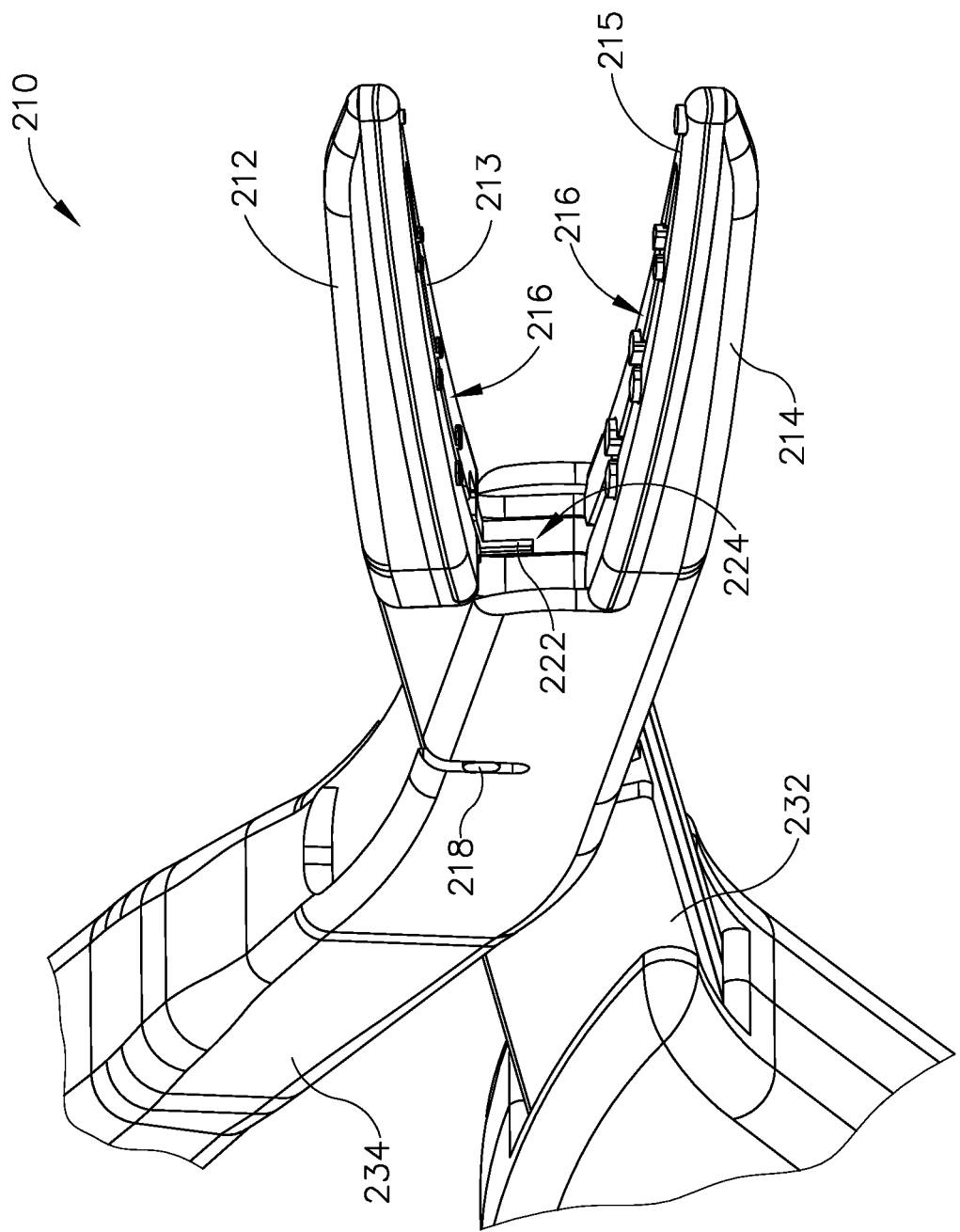
FIG. 6 depicts a perspective view of the end effector of FIG. 5 in an open position.
Figure 7:
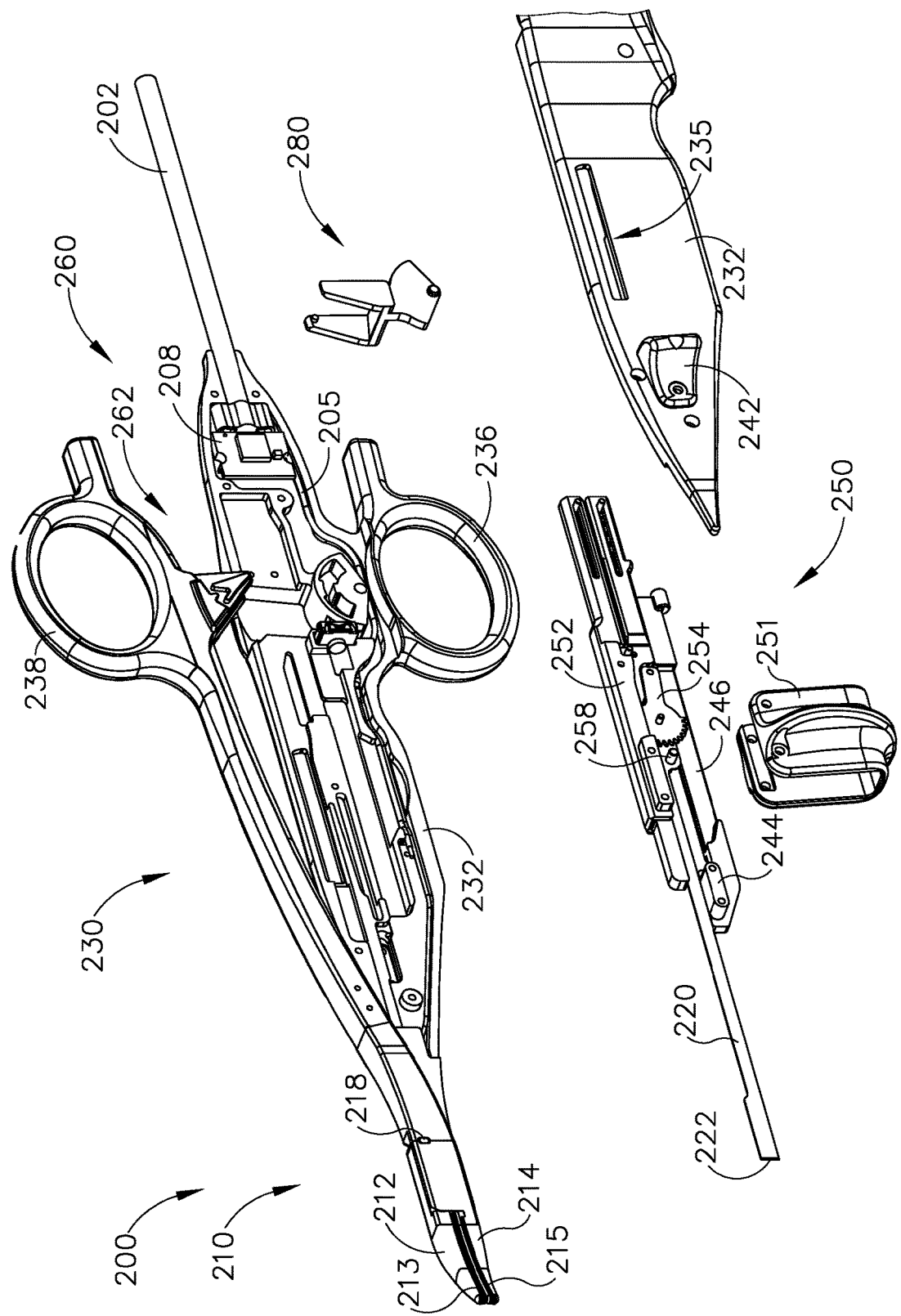
FIG. 7 depicts an exploded perspective view of instrument of FIG. 5 having a latching assembly.

First jaw (212) and second jaw (214) are pivotably coupled with each other via pivot pin (218). First jaw (212) and second jaw (214) may pivot between an open position (FIG. 6) and a closed position (FIG. 5) in order to grasp tissue. First and second electrodes (213, 215) are positioned on respective jaws (212, 214) such that electrodes (213, 215) face each other when jaws (212, 214) are pivoted into the closed position. Additionally, each electrode (213, 215) is U-shaped in the present example, with the bend of the U-shape located near the distal end of each respective jaw (212, 214), such that each electrode (213, 215) includes two longitudinally extending, laterally spaced-apart legs extending along the length of each respective jaw (212, 214). Laterally spaced-apart legs of each electrode (213, 215) and corresponding portions of jaws (212, 214) define an elongate slot (216). Elongate slot (216) is dimensioned to slidably receive knife (220) such that knife may translate from a proximal position to a distal position, similar to knife (120) described above. As best shown in FIG. 7, knife (220) includes a distal cutting edge (222) configured to sever tissue captured between jaws (212, 214) in the closed position.

A cable (202) extends proximally from handle assembly (230). Similar to cable (102) of instrument (100), cable (202) is configured to couple with control unit (104), which is further coupled with a power source (106). Therefore, control unit (104) is operable to provide RF power to electrodes (213, 215) of jaws (212, 214), to thereby seal tissue suitably captured between jaws (212, 214).

Handle assembly (230) includes a housing (232) and a resilient arm (234). Housing (232) and resilient arm (234) are substantially similar to housing (122) and resilient arm (134) described above, with differences elaborated below. Housing (232) and resilient arm (234) are pivotably coupled with each other via pivot pin (218). Housing (232) extends distally into first jaw (212), while resilient arm (234) extends distally into second jaw (214). Housing defines a knife pathway (224) that slidably houses a portion of knife (220). Housing (232) includes a finger ring (236) while resilient arm (234) terminates proximally into a thumb ring (238). Therefore, the operator may grasp instrument (200) in a scissor grip fashion and pivot resilient arm (234) relative to housing (232) via rings (236, 238) in order to open and close jaws (212, 214). Thumb ring (239) includes an arm portion (262) of latching assembly (260).

Resilient arm (234) is sufficiently resilient such that arm (234) may flex from a relaxed position to a flexed position in response to pivoting arm (234) further toward housing (232) when jaws (212, 214) are already in the closed position (similar to resilient arm (134) shown in FIGS. 3B-3C). Resilient arm (234) is biased toward the relaxed position. Further pivoting of resilient arm (234) into the flexed position may result in greater closure forces between jaws (212, 214) as compared to pivoting jaws (212, 214) into the closed position while arm (234) is in the relaxed position. Resilient arm (234) may be suitably resilient such that when resilient arm (234) is pivoted into the flexed position, the closure force between jaws (212, 214) is sufficient such that electrodes (213, 215) may properly seal tissue grasped between jaws (212, 214). Additionally, the resilient nature of arm (234) may limit the amount of closure force between jaws (212, 214) such that jaws (212, 214) may not compress tissue too much, resulting in inadvertent tissue damage.

Housing (232) contains electrode activation assembly (240), firing assembly (250), and locking body (280) of latching assembly (260). Firing assembly (250) of the current example includes a knife trigger (251) slidably coupled with housing (232) via a slot (235). As will be described in greater detail below, electrode activation assembly (240) is configured to selectively activate electrodes (213, 215); firing assembly (250) is configured to actuate knife (220) between the proximal position and the distal position (Similar to knife (120) as shown in FIGS. 4A-4B) in response to proximal translation of knife trigger (251) within slot (235); and latching assembly (260) is configured to selectively latch resilient arm (234) in the flexed position. Latching assembly (260) may also be configured to prevent actuation of knife (220) until specific conditions are satisfied. Additionally, latching assembly (260) may be configured to indicate when jaws (212, 214) are sufficiently closed to suitably seal tissue, and/or prevent activation of electrodes (213, 215) until specific conditions are satisfied.

Electrode activation assembly (240) includes an RF trigger (242) slidably supported on each lateral side of housing (232), a sliding body (246) slidably contained within housing (232), a coupling block (244) fixed relative to sliding body (246), an activation button (248), and a closure button (245). Coupling block (244) is configured to couple with each RF trigger (242) when instrument (200) is assembled. A proximal end of sliding body (246) is directly adjacent to activation button (248) such that proximal translation of sliding body (246) triggers activation button (248). Therefore, the operator may press RF trigger (242) proximally in order to compress activation button (248). RF trigger (242), coupling block (244), and/or sliding body (246) may be biased toward a position such that activation button (238) is not activated.

Activation button (248) and closure button (245) are each contained within housing (232). Closure button (245) and activation button (248) are each in communication with a circuit board (208) via electrical coupling wires (205); while circuit board (208) is also in communication with at least one electrode (213, 215) via electrical coupling wires (205). In the present example, circuit board (208) is contained within housing (232). Circuit board (208) is in communication with cable (202) such that circuit board (208) and control unit (104) are in electrical communication with each other. Therefore, circuit board (208) is configured to transfer RF energy from control unit (104) to electrodes (213, 215). As will be described in greater detail below, latching assembly (260) is configured to depress closure button (245) when jaws (212, 214) are sufficiently closed to provide sufficient closure force to properly seal tissue captured between electrodes (213, 215) using RF energy.

In one example, activation button (248) and closure button (245) are configured to instruct circuit board (208) to transfer RF energy from control unit (104) to electrodes (213, 215) when buttons (245, 248) are depressed. If only one, or neither, button (245, 248) is depressed, circuit board (208) will not transfer RF energy to electrodes (213, 215), thereby leaving electrodes (213, 215) deactivated. Therefore, for example, if the operator pressed RF trigger (242) without having closure button (245) depressed, electrodes (213, 215) will remain deactivated. Alternatively, closure button (245) may act as a switch for activation button (248) such that activation of closure button (245) completes a circuit between at least one electrode (213, 215) and activation button (248).

In another example, closure button (245) may only generate a signal to circuit board (208), which may then send the signal to control unit (104), that jaws (212, 214) are sufficiently closed to provide sufficient closure force to properly seal tissue captured between electrodes (213, 215) using RF energy. Control unit (104) may then signal to the operator (i.e. visually, audibly, or tactilely) that jaws (212, 214) are sufficiently closed. In such examples, activation button (248) may independently instruct circuit board (208) to transfer RF energy from control unit (104) to electrodes (213, 215) when activation button (248) is depressed.

In another example, depression of either activation button (248) or closure button (245) may be configured to activate electrodes (213, 215), but activation of buttons (245, 248) may send a different signal to control unit (104), such that control unit produces a different signal (i.e. visually, audibly, or tactilely) indicating to a user which button (245, 248) has been depressed.

In yet another example, activation button (248) may be omitted entirely such that pressing closure button (245) leads to activation of electrodes (213, 215).

Firing assembly (250) of the current example includes a knife trigger (251) slidably coupled with housing (232) via slot (235), an input rack (252), a rotary drive (254), a link (256), and an output body (258). Input rack (252) includes a lockout ledge (255). As will be described in greater detail below, lockout ledge (255) is configured to prevent proximal translation of input rack (252), which in turn prevents the firing of knife (220), when latching assembly (260) does not latch jaws (212, 214) in the closed position with reselling arm (234) in the flexed position in accordance with the description herein.

Input rack (252) is slidably contained within housing (232). In particular, input rack (252) is associated with knife trigger (251) such that movement of knife trigger (251) in one direction may lead to movement of input rack (252) in the same direction. Rotary drive (254) is rotatably coupled with housing (232) such that rotary drive (254) may rotate relative to housing (232), but rotary (254) may not translate relative to housing (232). Output body (258) slidably housed within housing (232) via a pin (259). In particular, pin (259) is fixed relative to output body (258), while a portion of pin (259) is slidably disposed within a firing slot (257) defined by the interior of housing (232). Additionally, output body (258) is associated with knife (220) such that movement of output body (258) drives movement of knife (220). Link (256) is pivotably coupled to both rotary drive (254) as well as output body (258).

Figure 12A:
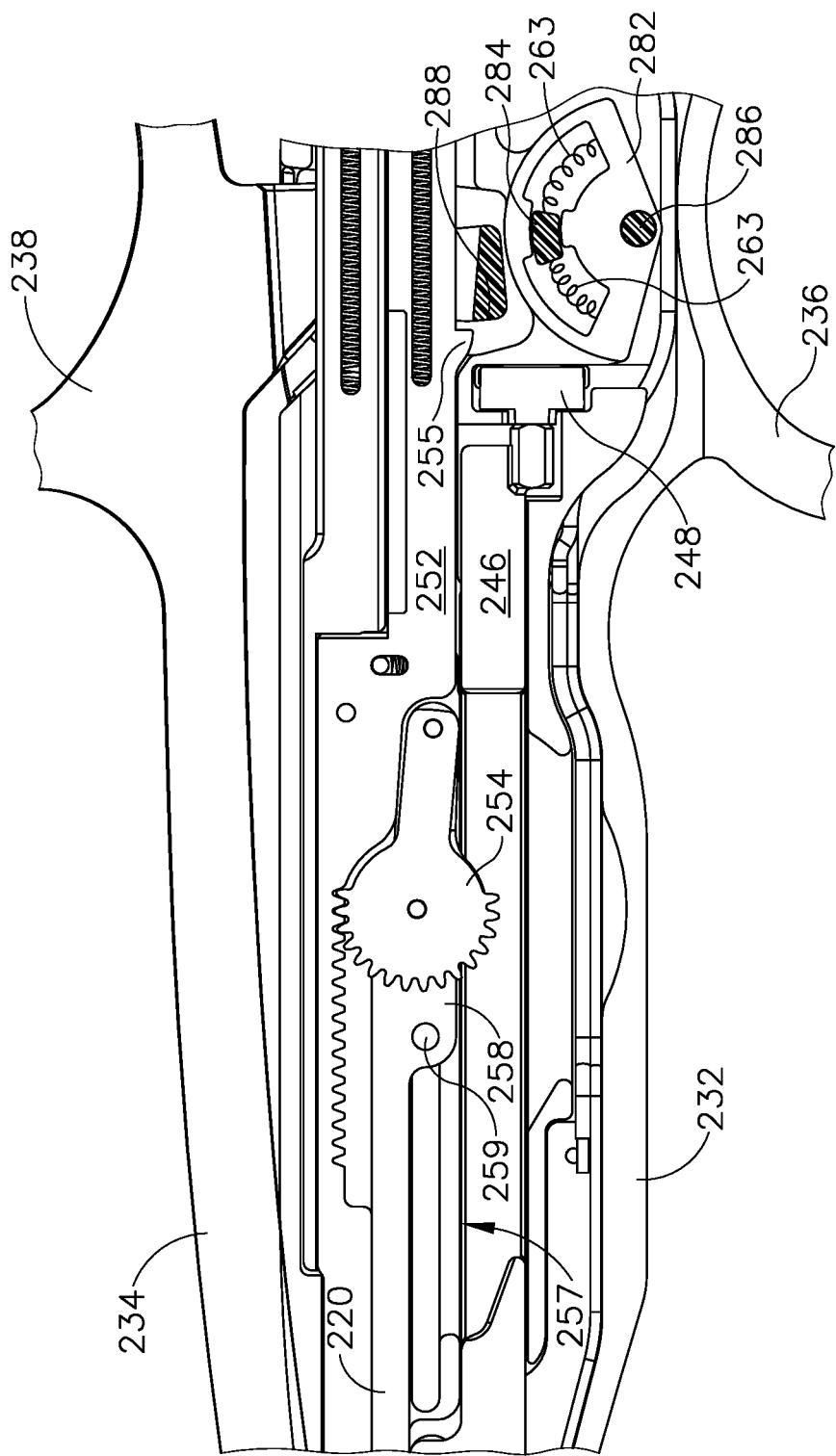
FIG. 12A depicts a cross-sectional view of a portion of the handle assembly of FIG. 8, taken along line 10-10 of FIG. 5, where the latching assembly is in the latched configuration, where the firing assembly is in the pre-fired position.
Figure 12B:
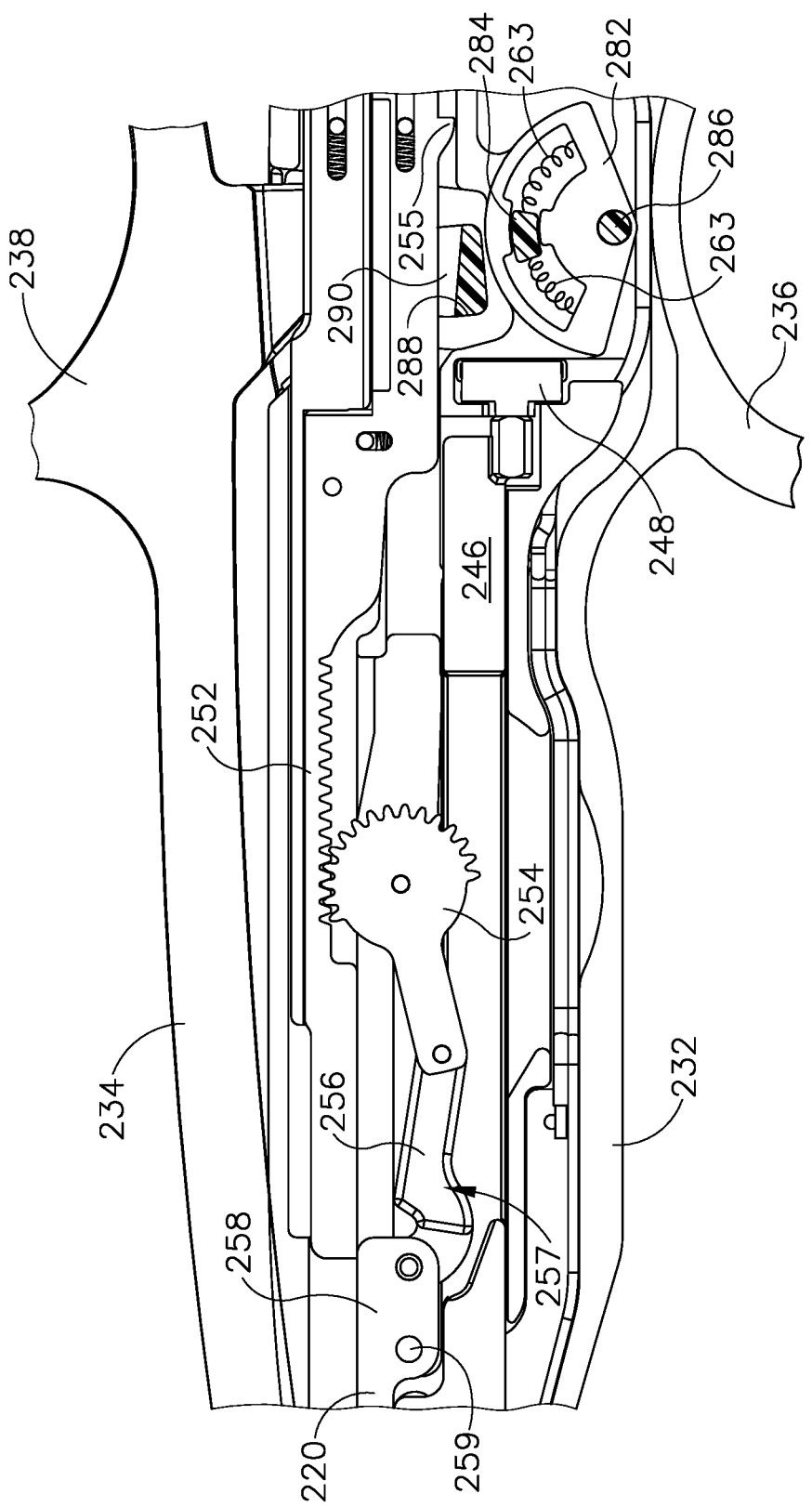
FIG. 12B depicts a cross-sectional view of a portion of the handle assembly of FIG. 8, taken along line 10-10 of FIG. 5, where the latching assembly is in the latched configuration, where the firing assembly is in a fired position.

Input rack (252) meshes with a portion of rotary drive (254) such that translation of input rack (252) causes rotation of rotary drive (254). FIG. 12A shows firing assembly (250) in a position associated with knife (220) being in the pre-fired position. If the operator desires to fire knife (220) through jaws (212, 214) while jaws (212, 214) are in the closed position in accordance with the description herein, the operator may proximally drive knife trigger (251) such that input rack (252) is also driven proximally. As shown in FIG. 8B, input rack (252) may rotate rotary drive (254) in a first angular direction, causing rotary drive (254) to rotate link (256) relative to both rotary drive (254) and output body (258). Because output body (258) is slidably constrained in a linear direction via pin (259) and firing slot (257), rotation of link (256) relative to rotary drive (254) actuates output body (258) and knife (220) distally such that knife (220) actuates distally within jaws (212, 214) toward the fired position. In other words, proximally translation of knife trigger (251) is configured to distally fire knife (220). Knife trigger (251) or input rack (252) may be biased toward the distal position shown in FIG. 12A such that after the operator actuates knife trigger (251) proximally to fire knife (220), the operator may let go of knife trigger (251) such that input rack (252) rotates rotary drive (254) in the second, opposite, angular direction, thereby driving output body (258) and knife (220) proximally into the pre-fired position. results in distal translation of knife (220).

While firing assembly (250) of the current example includes a rack, pinion, and link configuration, any suitable firing assembly may be used in replacement of firing assembly (250) described above that would be apparent to one having ordinary skill in the art in view of the teachings herein.

As mentioned above, and as will be described in greater detail below, latching assembly (260) is configured to selectively latch resilient arm (234) in the flexed position. Latching assembly (260) may also be configured to prevent actuation of knife (220) until specific conditions are satisfied. Additionally, latching assembly (260) may be configured to depress closure button (245) when latching resilient arm (234) in the flexed position such that closure button (245) operates in accordance with the description herein.

Figure 8:
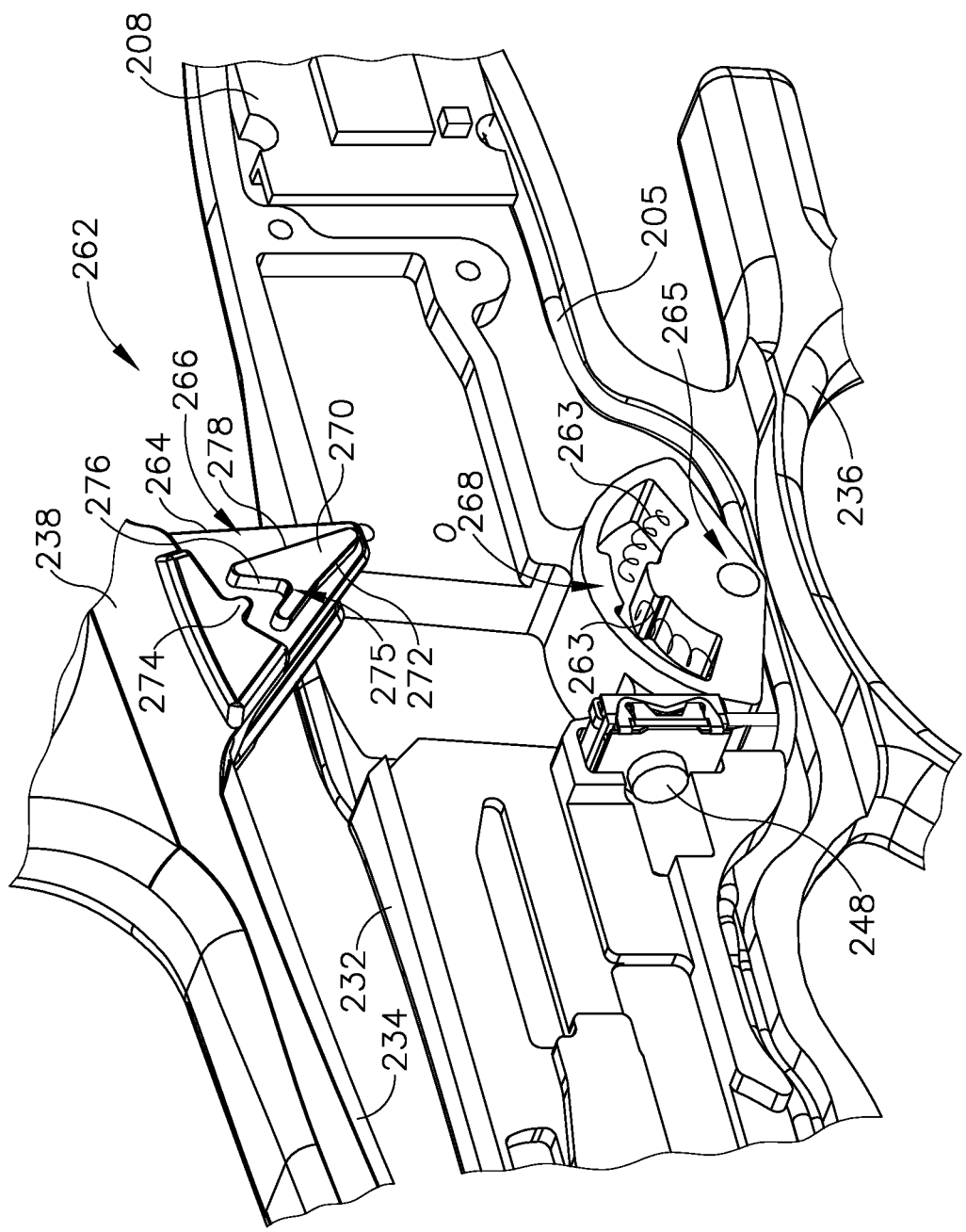
FIG. 8 depicts a perspective view of a portion of a handle assembly of the instrument of FIG. 5, with certain portions omitted for clarity, and an arm portion of the latching assembly of FIG. 7.

Latching assembly (260) includes arm portion (262) and locking body (280). As best seen in FIG. 8, arm portion (262) includes a downward protrusion (264) extending from thumb ring (238). Downward protrusion (264) defines a gap such that as resilient arm (234) is flexed, downward protrusion (264) does not interfere with input rack (252) of firing assembly (250). On each lateral side, downward protrusion (264) includes a laterally presented protrusion (270) and a nub (274). Each laterally presented protrusion (270) includes a first cam surface (272), a second cam surface (276), and a third cam surface (278). Additionally, laterally presented protrusions (270) and respective nubs (274) define a recessed path (266) and a latch pocket (275).

Figure 10:
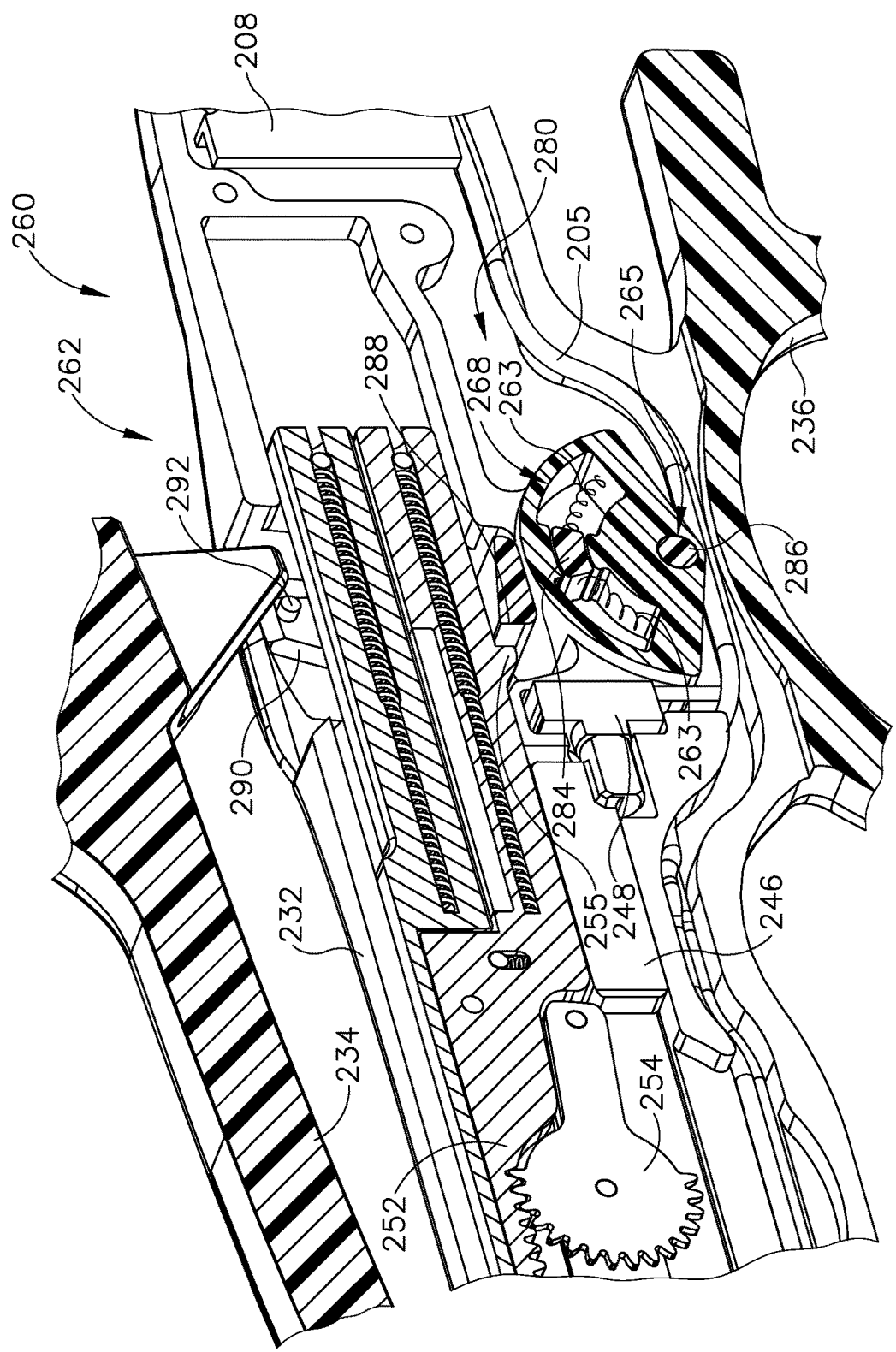
FIG. 10 depicts a cross-sectional view of the handle assembly of FIG. 8, taken along line 10-10 of FIG. 5, where a firing assembly is in a pre-fired position, where the latching assembly is in an unlatched configuration.
Figure 11A:
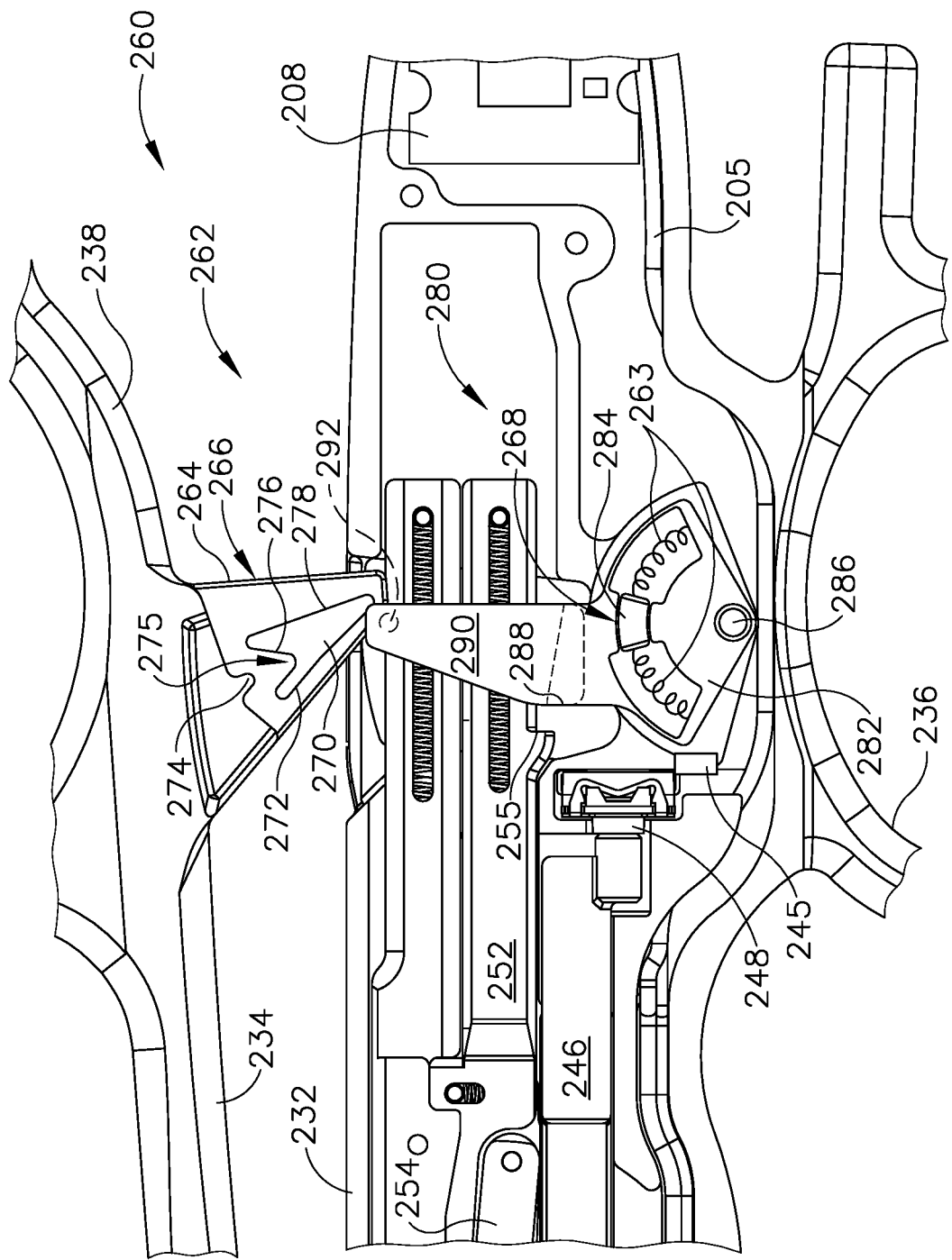
FIG. 11A depicts an elevational side view of a portion of the handle assembly of FIG. 8, with a portion of the handle assembly omitted for clarity, where the resilient arm is in the relaxed position, where the latching assembly is in the unlatched configuration.

Housing (232) defines a pivot hole (265), and a guided path (268). Guided path (268) houses two bias members (263). Pivot hole (265) is dimensioned to receive a pivot pin (286) of locking body (280) such that locking body (280) is pivotably connected to housing (232). As best seen in FIG. 10, guided path (268) is dimensioned to house a biasing projection (284) of locking body (280) such that as locking body (280) pivots relative to housing (232), biasing projection (284) actuated within guided path (268). Additionally, biasing projection (284) is configured to abut against both bias members (263) such that bias members (263) resiliently bias locking body (280) to a first position (as shown in FIGS. 10-11A). While in the current example, biasing members (263) are springs, any other suitably biasing member may be utilized as would be apparent to one having ordinary skill in the art in view of the teachings herein.

Figure 9:
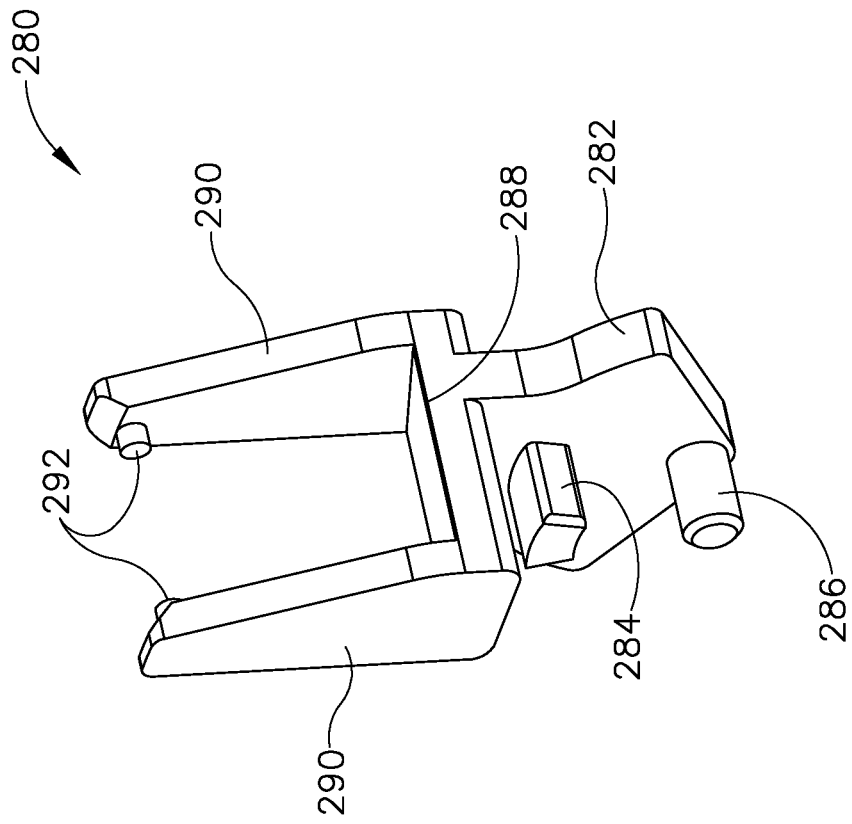
FIG. 9 depicts a perspective view of a locking body of the latching assembly of FIG. 7.

As best seen in FIG. 9, locking body (280) includes a base member (282), biasing projection (284), pivot pin (286), a lockout ledge (288), a pair of arms (290), and a respective catch projection extending laterally inward from each arm (290). Pivot pin (286) and biasing projection (284) extend laterally from base member (282). As mentioned above, pivot pin (286) pivotably couples locking body (280) with housing (232), while biasing projection (284) abuts against biasing members (263) to bias locking body (280) toward a first position. Additionally, lockout ledge (288) extends laterally across the top of base member (282), while an arm (290) extends upwardly from lockout ledge (288). Arms (290) and lockout ledge (288) define a U-shaped gap dimensioned to receive input rack (252) of firing assembly (250) and downward protrusion (264).

As will be describe in greater detail below, cam surfaces (272, 276, 278) of laterally presented protrusion (270) and nub (274) are configured to selectively contact a respective catch protrusion (292) of locking body (280) such that flexing of resilient arm (234) moves locking body (280) between an un-latched configuration and a latched configuration. As will be described in greater detail below (280), base member (282) is configured to depress closure button (245) when latching assembly (260) latches resilient arm (234) in the flexed position. As will also be described in greater detail below, lockout ledge (288) is configured to prevent firing of firing assembly (250) while latching assembly (260) is in the un-latched position; while allowing firing of firing assembly (250) while latching assembly (260) is in the latched position.

FIGS. 11A-11H show an exemplary use of latching assembly (260) in order to latch and un-latch resilient arm (234) in the flexed position such that jaws (212, 214) are sufficiently closed to suitably seal tissue. As will be described in greater detail below, the operator may latch resilient arm (234) in the flexed position by pressing thumb ring (238) toward housing (232) whiles jaws (212, 214) are already in the closed position; while the operator may further unlatch resilient arm (234) to by again pressing thumb ring (238) toward housing while latching assembly (260) is in the latched configuration.

First, as shown in FIG. 11A, resilient arm (234) is pivoted relative to housing (232) such that resilient arm (234) is in the relaxed position while jaws (212, 214) are in the closed position. With jaws (212, 214) in the closed position, tissue may be grasped between the confines of jaws (212, 214). At this point, biasing members (263) abut against biasing projection (284) to keep locking body (280) in the first position. With resilient arm (234) in the relaxed position, the closure forces may not be suitable for sealing tissue between jaws (212, 214). Therefore, base member (282) does not depress closure button (245) of activation assembly such that closure button (245) is not activated. Lockout ledge (288) is adjacent to lockout ledge (255) of input rack (252) such that if the operator attempted to proximally actuate knife trigger (251) to fire knife (220) distally, lockout ledges (255, 288) may abut against each other to help prevent firing of knife (220).

Figure 11B:
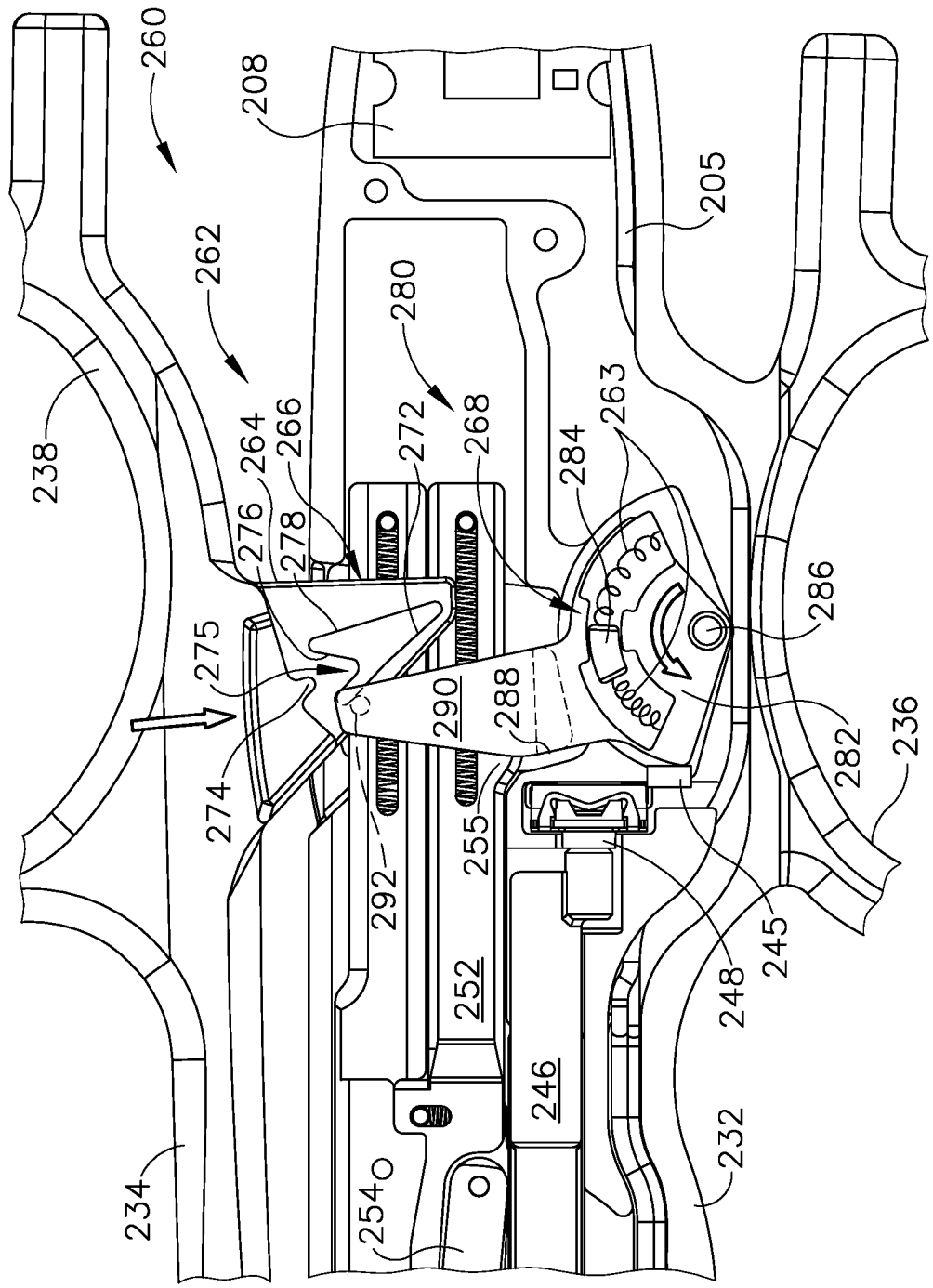
FIG. 11B depicts an elevational side view of a portion of the handle assembly of FIG. 8, with a portion of the handle assembly omitted for clarity, where the resilient arm is in a flexed position, where the latching assembly is in a first pre-latched configuration.
Figure 11C:
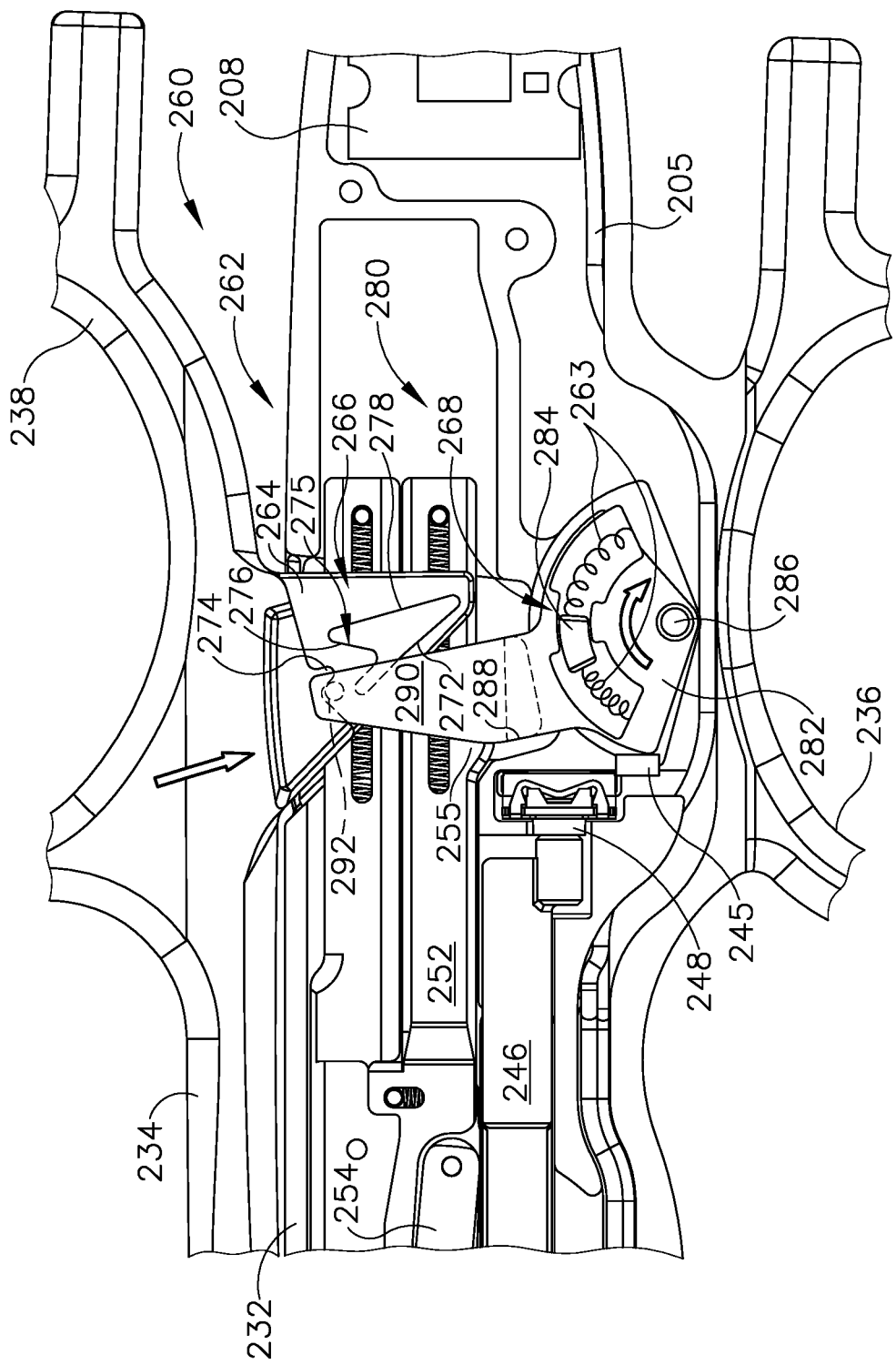
FIG. 11C depicts an elevational side view of a portion of the handle assembly of FIG. 8, with a portion of the handle assembly omitted for clarity, where the resilient arm is in the flexed position, where the latching assembly is in a second pre-latched configuration.

When the operator desires to latch resilient arm (234) in the flexed position, such as for sealing tissue via electrodes (213, 215) with a suitable closure force provided by jaws (212, 214), the operator may further pivot thumb ring (238) toward housing (232). FIG. 11B shows the operator initially actuating thumb ring (238) toward housing (232), thereby flexing resilient arm (234). Initial flexing of resilient arm (234) from the unlatched position toward the latched position causes first cam surface (272) to abut against catch protrusion (292). As thumb ring (238) actuates downward, contact between first cam surface (272) and catch protrusion (292) overcomes the biasing force provided by biasing members (263) such that locking body (280) pivots in a first angular direction. As best seen between FIGS. 11B-11C, further downward actuation of thumb ring (238) causes first cam surface (272) to lose contact with catch protrusion (292) such that biasing members (263) push biasing projection (284) in the second angular direction to rotate locking body (280) back toward the first, biased, position. However, catch protrusions (292) travel within recessed path (266) such that protrusions (292) make contact with nub (274) before locking body (280) reaches the first, biased, position. At this moment, contact between protrusions (292) and nub (274) may prevent further downward actuation of thumb ring (238). It should be understood that at the moment shown in FIG. 11C, the operator is applying the force to keep resilient arm in the flexed position.

Figure 11D:
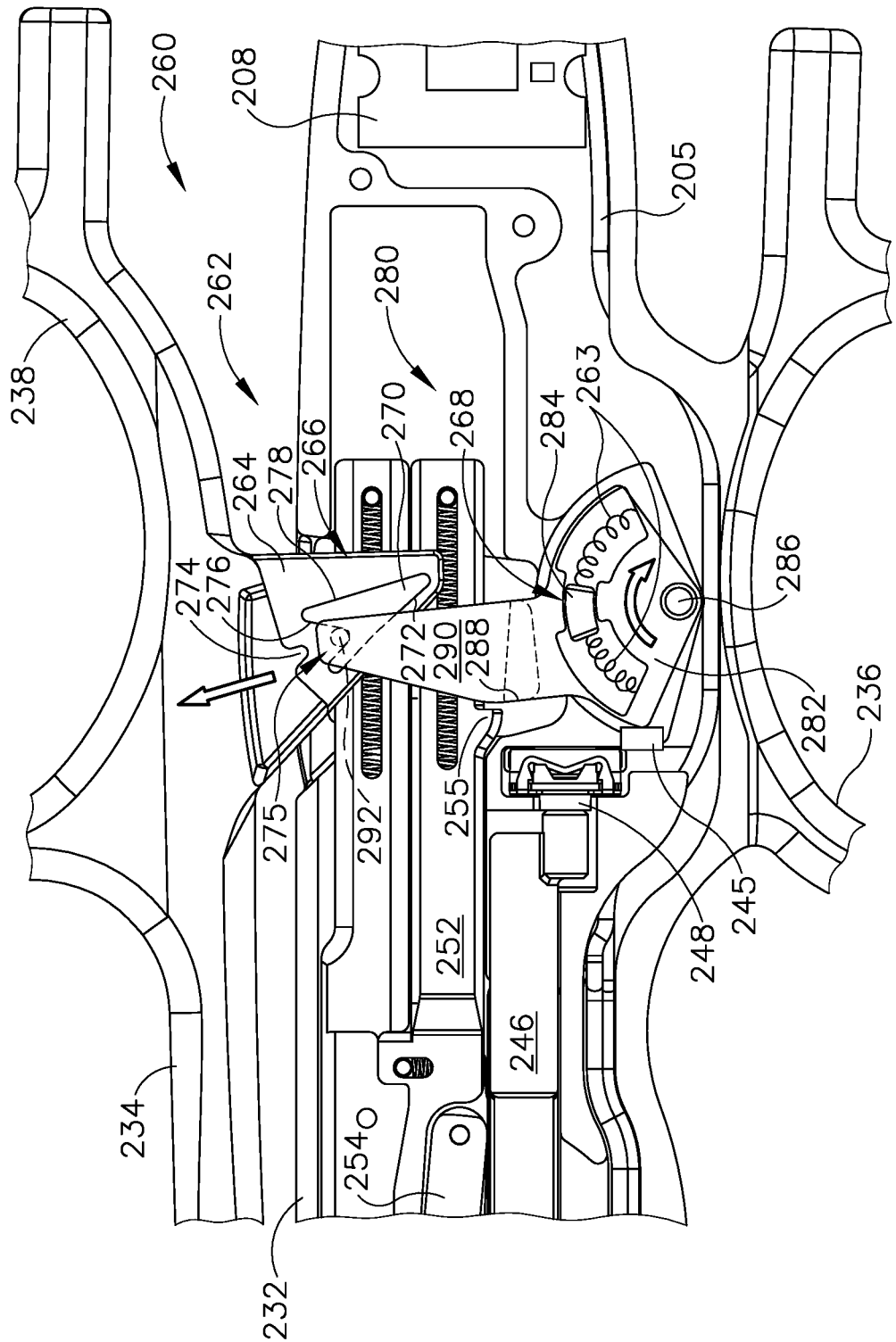
FIG. 11D depicts an elevational side view of a portion of the handle assembly of FIG. 8, with a portion of the handle assembly omitted for clarity, where the resilient arm is in the flexed position, where the latching assembly is in a latched configuration.

Next, as shown in FIG. 11D, the operator may release or otherwise reduce the amount of downward force on thumb ring (238), such that the resilient nature of arm (234) causes thumb thing (238) and arm portion (262) of latch assembly (260) to actuate away from housing (232). With arm portion (262) actuating away from housing (232), nub (274) no longer makes contact with protrusions (292), thereby allowing biasing members (263) to actuate biasing projection (284) and locking body (280) in the second angular direction until catch protrusions (292) rest within latch pocket (275). When catch protrusions (292) rest within the latch pocket (275), latch assembly (260) is in the latched configuration. It should be understood that at this point, resilient arm (234) is in the flexed position such that jaws (212, 214) are sufficiently closed to suitably seal tissue. With protrusions (292) resting within latch pocket (275), contact between catch protrusions (292) of lock body (280) and protrusions (270) of arm portion (262) prevent any further movement of thumb ring (238) away from housing (232), effectively latching resilient arm (234) in the flexed position. In the latched position shown in FIG. 11D, the operator may no longer need to press down on thumb ring (238) or other portions of resilient arm (234) in order to keep resilient arm (234) in the flexed position. In other words, when latch assembly (260) is in the latched configuration, resilient arm (234) may remain in the flexed position without assistance from the operator such that jaws (212, 214) provide a suitable closure force for adequately sealing tissue.

Regarding activation assembly (240), base member (282) depresses closure button (245) when latch assembly (260) is in the latched configuration such that closure button (245) is activated. With closure button (245) activated, electrode activation assembly (240) may operate as described in accordance with any of the descriptions herein. Additionally, or alternatively, depressing closure button (245) may allow closure button (245) to indicate that latching assembly (260) is in the latched configuration. For instance, closure button (245) may generate a signal to control unit (104) such that control unit (104) may indicate to the operator that latching assembly (260) is successfully in the latched configuration.

Regarding firing assembly (250) lockout ledge (288) of locking body (280) is bellow lockout ledge (255) of input rack (252) when latch assembly (260) in the latched configuration. Therefore, lockout ledge (288) of locking body (280) no longer interferes with proximal translation of lockout ledge (255) of input rack (252). In other words, with latch assembly (260) in the latched configuration, the operator may actuate firing assembly (250) to actuate knife (220) between the pre-fired and fired positions.

Figure 11E:
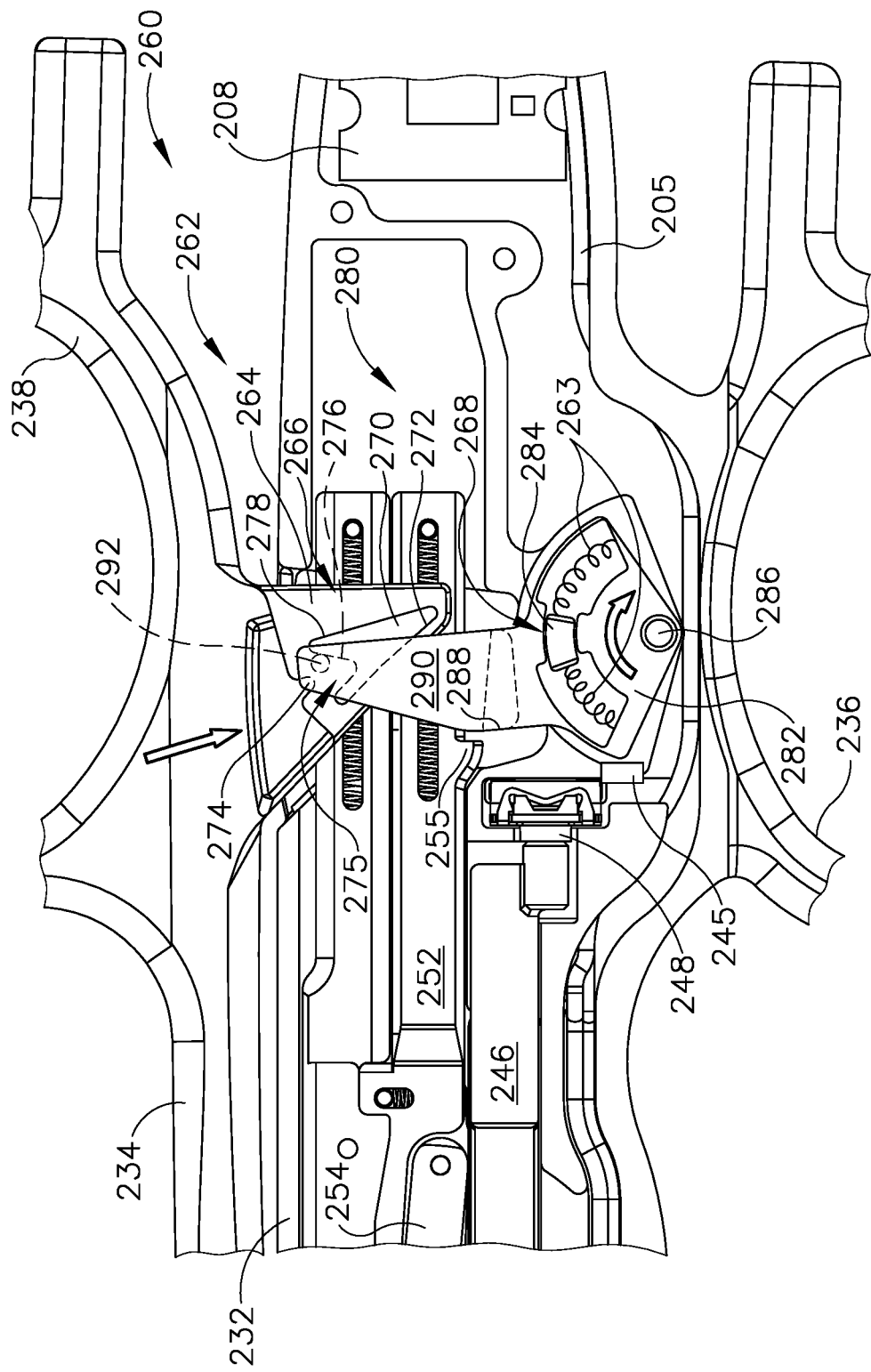
FIG. 11E depicts an elevational side view of a portion of the handle assembly of FIG. 8, with a portion of the handle assembly omitted for clarity, where the resilient arm is in the flexed position, where the latching assembly is in a first post-latched configuration.

When the operator decides to unlatch latching assembly (260) such that resilient arm (234) may resiliently return to the relaxed position, the operator may push thumb ring (238) toward housing (232). As shown in FIG. 11E, when the operator initially pushes thumb ring (238) toward housing (232) while latching assembly (260) is in the latched position, biasing members (263) may push biasing projection (284) in the second angular direction such that catch protrusions (292) stay in contact with second camming surface (276). In other words, as thumb ring (238) actuates toward housing (232) to unlatch latching assembly (260), catch protrusions (292) ride along second camming surface (276).

Figure 11F:
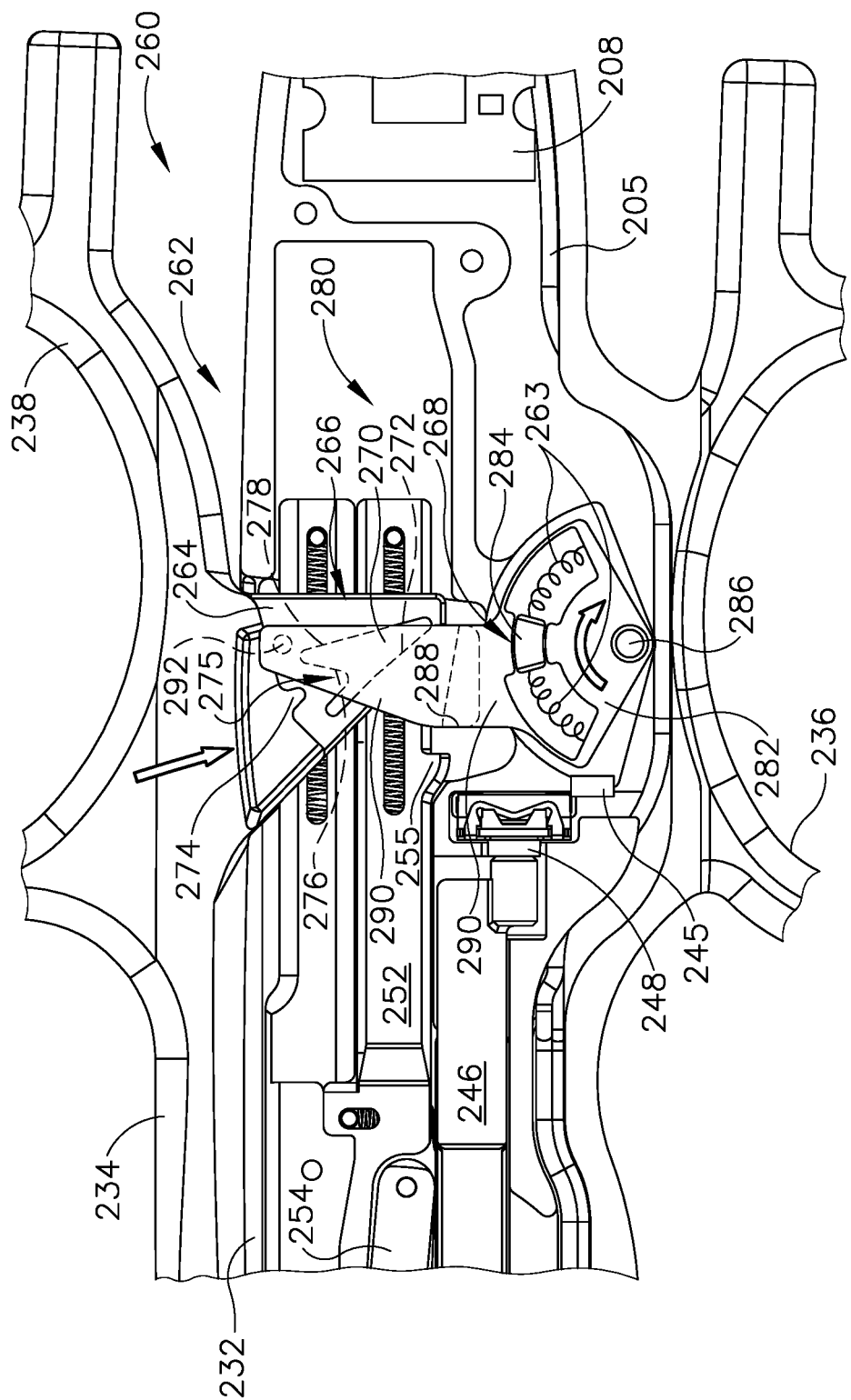
FIG. 11F depicts an elevational side view of a portion of the handle assembly of FIG. 8, with a portion of the handle assembly omitted for clarity, where the resilient arm is in the flexed position, where the latching assembly is in a second post-latched configuration.
Figure 11G:
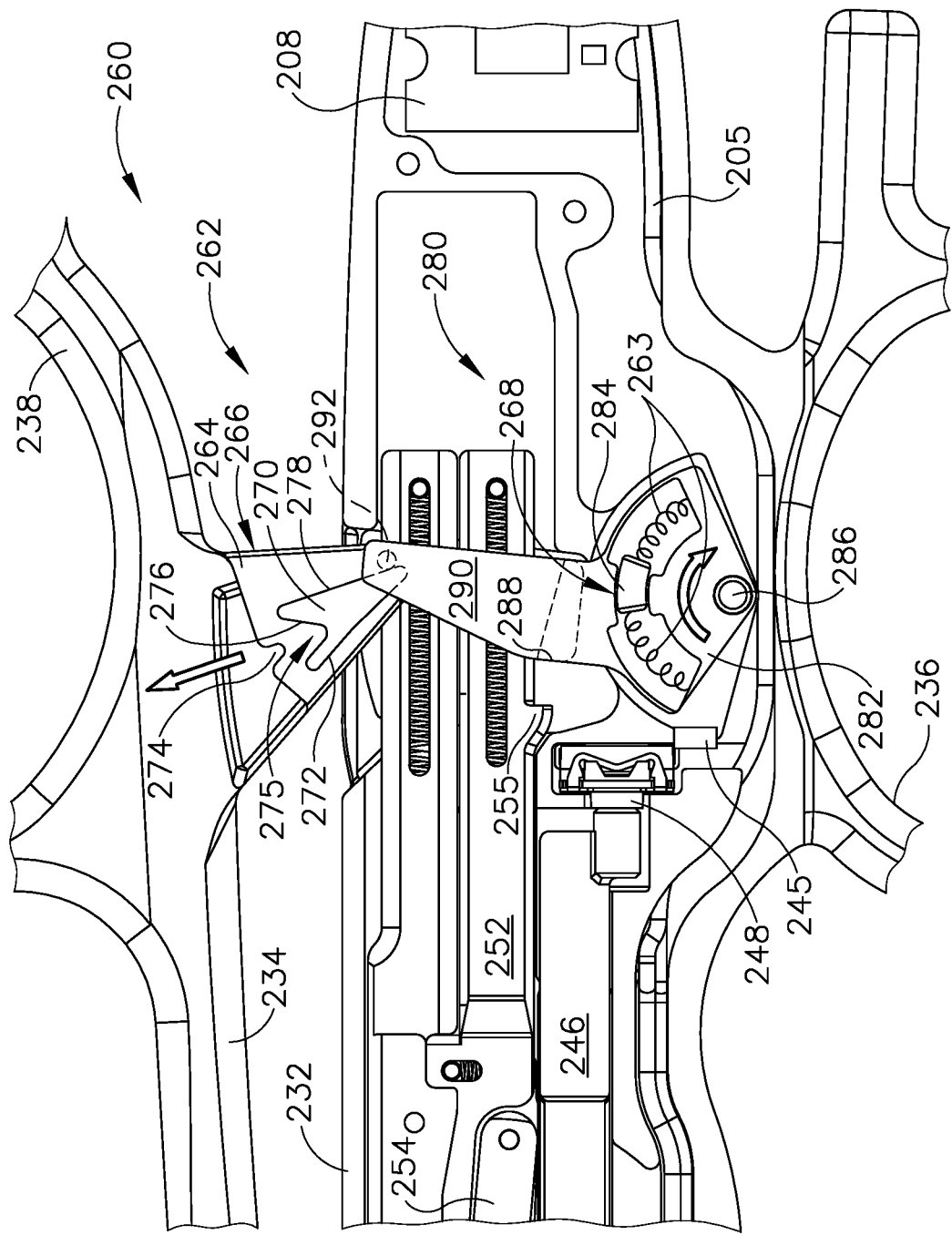
FIG. 11G depicts an elevational side view of a portion of the handle assembly of FIG. 8, with a portion of the handle assembly omitted for clarity, where the resilient arm is in the flexed position, where the latching assembly is in a third post-latched configuration.
Figure 11H:
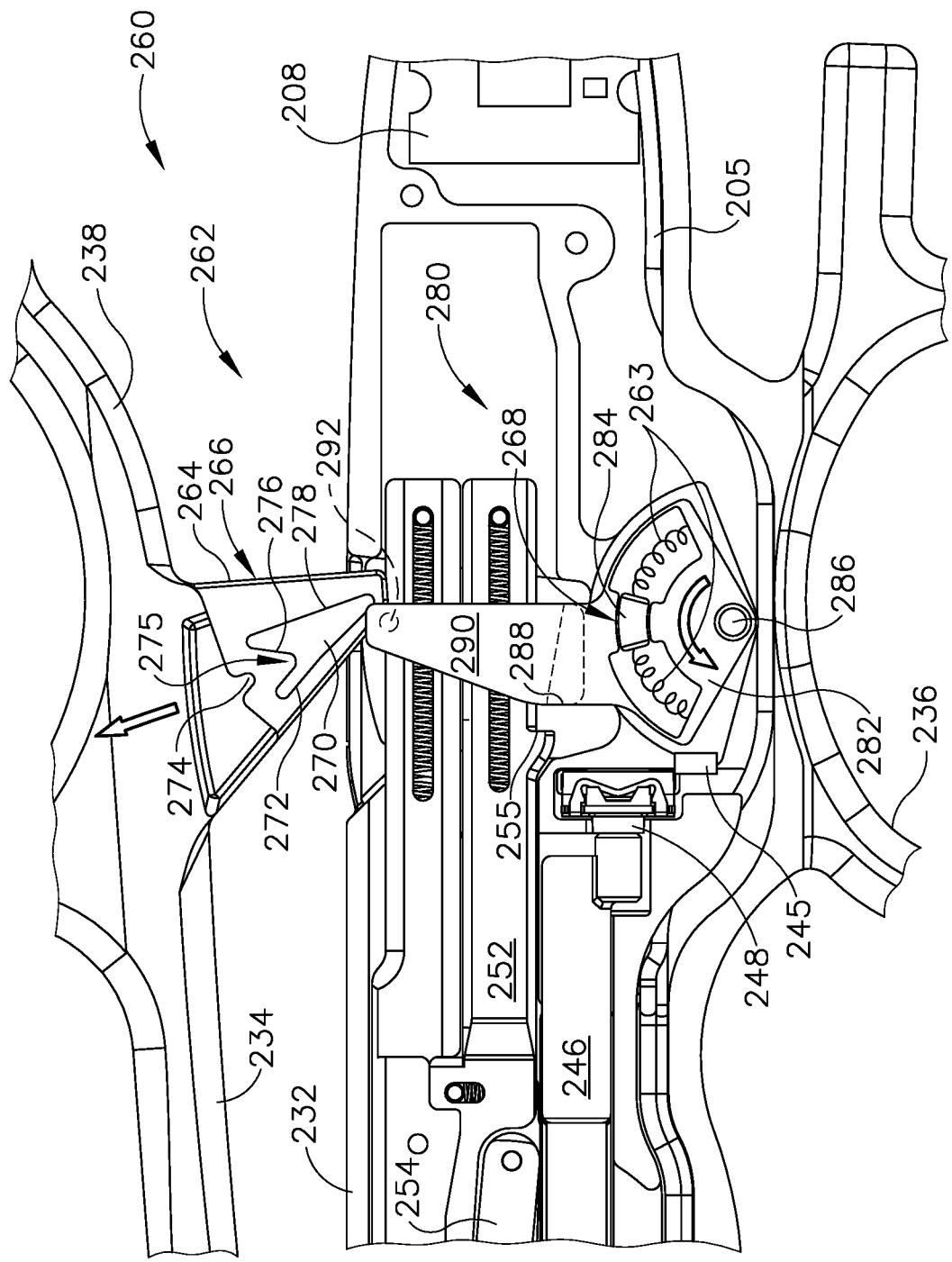
FIG. 11H depicts an elevational side view of a portion of the handle assembly of FIG. 8, with a portion of the handle assembly omitted for clarity, where the resilient arm is in the relaxed position, where the latching assembly is returned to the unlatched configuration.

As shown in FIG. 11F, the operator may further thumb ring (238) toward housing (232) until catch protrusions (292) are no longer in contact with second cam surface (276). At this moment, catch protrusions (292) are no longer in contact with any element of arm portion (262). Therefore, biasing members (263) actuate biasing projection (284) and the rest of locking body (280) into the first, biased, position. However, resilient arm (234) is still in the flexed position such that protrusion (270) is underneath catch projection (292). Therefore, it should be understood that at the moment shown in FIG. 11F, the operator is holding resilient arm (234) in the flexed position. As best shown between FIGS. 11F-11H, if the operator releases resilient arm (234) or otherwise reduces the force holding resilient arm (234) in the flexed position, the resilient nature will bend arm (234) back into the relaxed position. As resilient arm (234) returns to the flexed position between FIGS. 11F-11H, catch protrusions (292) will contact third cam surface (278), which in turn drives locking body (280) in the second angular direction.

Once resilient arm (234) completely returns to the relaxed position while jaws (212, 214) are still in the closed position, catch protrusion (292) of locking body (280) will no longer be in contact with third cam surface (278) such that arm portion (262) of latch assembly (260) returns to the unlatched configuration. Biasing member (263) returns locking body (280) to the first position while arm portion (262) is placed above catch protrusion (292) such that first cam surface (272) is adjacent to catch protrusion (292). In the unlatched configuration, the operator may further open jaws (212, 214) by pivoting resilient arm (234) away from housing (232); or the operator may re-latch resilient arm (234) in accordance with the description above.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position; and (c) a latch assembly configured to transition between an unlatched configuration and a latched configuration, wherein the latch assembly is configured to prevent the arm from pivoting the second jaw from the closed position toward the open position in the latched configuration, wherein the latch assembly is configured to allow the arm to pivot the second jaw from the closed position toward the open position in the unlatched configuration.

Example 2

The surgical instrument of Example 1, wherein the latch assembly comprises a lockout ledge, wherein the lockout ledge is configured to prevent distal actuation of the knife while the latch assembly is in the unlatched configuration, wherein the lockout ledge is configured to allow distal actuation of the knife while the latch assembly is in the latched configuration.

Example 3

The surgical instrument of any one or more of Examples 1 through 2, further comprising a closure button, wherein the closure button is configured to generate a signal in response in response to the latch assembly transitioning into the latched configuration.

Example 4

The surgical instrument of any one or more of Example 1 through 3, wherein the arm comprises a resilient member, wherein the resilient member is configured to transition between a relaxed configuration and a flexed configuration while the second jaw is in the closed configuration.

Example 5

The surgical instrument of Example 4, wherein the resilient member is configured to be in the flexed configuration while the latched assembly is in the latched configuration.

Example 6

The surgical instrument of any one or more of Examples 1 through 5, wherein the latch assembly comprises an arm portion associated with the arm, wherein the arm portion includes a projection.

Example 7

The surgical instrument of Example 6, wherein the latch assembly comprises a locking body, wherein the locking body is pivotably coupled with the housing.

Example 8

The surgical instrument of Example 7, wherein the projection is configured to pivot the locking body as the arm pivots toward the housing.

Example 9

The surgical instrument of Example 8, wherein the projection defines a latch pocket.

Example 10

The surgical instrument of Example 9, wherein the latch pocket is dimensioned to house a portion of the locking body while the latch assembly is in the latched configuration.

Example 11

The surgical instrument of Example 10, wherein the locking body is biased to an upward position.

Example 12

The surgical instrument of any one or more of Examples 1 through 11, wherein the arm is configured to transition the latch assembly between the latched configuration and the unlatched configuration.

Example 13

The surgical instrument of Example 12, wherein the arm is configured to actuate toward the housing in order to transition the latch assembly between the latched configuration and the unlatched configuration.

Example 14

The surgical instrument of any one or more of Examples 1 through 13, wherein the arm further comprises a thumb ring, wherein a portion of the latch assembly is coupled the thumb ring.

Example 15

The surgical instrument of any one or more of Examples 1 through 14, further comprising an electrode activation assembly comprising a trigger, wherein the trigger is configured to activate the electrode assembly.

Example 16

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position, wherein the arm is configured to pivot relative to the housing; and (c) a latching assembly comprising: (i) a locking body pivotably coupled with the housing, and (ii) a camming body associated with the arm, wherein the camming body is configured to pivot the locking body in response to actuating the arm relative to the housing in order transition the latching assembly between an unlatched configuration and a latched configuration, wherein the latching assembly is configured to prevent the arm from pivoting the second jaw from the closed position to the open position in the latched configuration.

Example 17

The surgical instrument of Example 16, herein the locking body comprises a catch protrusion, wherein camming body defines a latch pocket dimensioned to house the catch protrusion in the latched configuration.

Example 18

The surgical instrument any one or more of Examples 16 through 17, herein the locking body comprises a lockout surface configured to prevent distal actuation of the knife while the latching assembly is in the unlatched configuration.

Example 19

The surgical instrument of any one or more of Examples 16 through 18, wherein the locking body is biased to an upward position.

Example 20

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; and (b) a handle assembly, wherein the handle assembly comprises: (i) a housing associated with the first jaw, and (ii) an arm associated with the second jaw, wherein the arm is configured to pivot the second jaw between the open position and the closed position, wherein the arm is configured to pivot relative to the housing between a first position, a second position, and a third position, wherein the second jaw is configured to be in the open position while the arm is in the first position, wherein the second jaw is configured to be in the closed position while the arm is in the second position and the third position; and (c) a latching assembly configured to transition between an unlatched configuration and a latched configuration, wherein the latching assembly is configured to prevent the arm from pivoting the second jaw from the closed position to the open position in the latched configuration, wherein the latching assembly is configured to transition between the latched configuration and the unlatched configuration in response to the arm actuating between the second position and the third position.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/989,424, entitled "Method and Apparatus for Open Electrosurgical Shears," filed on May 25, 2018, published as U.S. Pub. No. 2019/0357962 on Nov. 28, 2019; U.S. application Ser. No. 15/989,430, entitled "Electrosurgical Shears with Knife Lock and Clamp-Actuated Switch," filed on May 25, 2018issued as U.S. Pat. No. 10,966,781 on Apr. 6, 2021; U.S. application Ser. No. 15/989,433, entitled "Knife Drive Assembly for Electrosurgical Shears," filed on May 25, 2018, published as U.S. Pat. No. 2019/0357963 on Nov. 28, 2019; U.S. application Ser. No. 15/989,438, entitled "Knife Auto-Return Assembly for Electrosurgical Shears," filed on May 25, 2018 issued as U.S. Pat. No. 10,898,259 on Jan. 25, 2021; U.S. application Ser. No. 15/989,422, entitled "Compound Screw Knife Drive for Electrosurgical Shears," filed on May 25, 2018, issued as U.S. Pat. No. 10,856,931 Dec. 8, 2020; U.S. application Ser. No. 15/989,488, entitled "Firing and Lockout Assembly for Knife for Electrosurgical Shears," filed on May 25, 2018 published as U.S. Pub. No. 2019/0357966 on Nov. 28, 2019; and U.S. application Ser. No. 15/989,452, entitled "Dual Stage Energy Activation for Electrosurgical Shears," filed on May 25, 2018published as U.S. Pub. No. 2019/035767 on Nov. 28, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. A surgical instrument comprising:
(a) an end effector, wherein the end effector comprises:
(i) a first jaw,
(ii) a second jaw pivotably coupled with the first jaw, wherein the second jaw is operable to move between an open position and a closed position,
(iii) a knife configured to actuate between a pre-fired position and a fired position, and
(iv) an electrode assembly configured to apply RF energy to tissue;
(b) a handle assembly, wherein the handle assembly comprises:
(i) a housing associated with the first jaw, and
(ii) an arm associated with the second jaw, wherein the arm is configured to pivot the second jaw between the open position and the closed position; and
(c) a latch assembly configured to transition between an unlatched configuration and a latched configuration, wherein the latch assembly is configured to prevent the arm from pivoting the second jaw from the closed position toward the open position in the latched configuration, wherein the latch assembly is configured to allow the arm to pivot the second jaw from the closed position toward the open position in the unlatched configuration, wherein the latch assembly comprises a lockout ledge pivotable relative to the housing and the arm, wherein the lockout ledge is configured to inhibit distal actuation of the knife while the latch assembly is in the unlatched configuration, wherein the lockout ledge is configured to allow distal actuation of the knife while the latch assembly is in the latched configuration.

2. The surgical instrument of claim 1, further comprising a closure button, wherein the closure button is configured to generate a signal in response to the latch assembly transitioning into the latched configuration.

3. The surgical instrument of claim 1, wherein the arm comprises a resilient member, wherein the resilient member is configured to transition between a relaxed configuration and a flexed configuration while the second jaw is in the closed position.

4. The surgical instrument of claim 3, wherein the resilient member is configured to be in the flexed configuration while the latched assembly is in the latched configuration.

5. The surgical instrument of claim 1, wherein the latch assembly comprises an arm portion associated with the arm, wherein the arm portion includes a projection.

6. The surgical instrument of claim 5, wherein the latch assembly comprises a locking body, wherein the locking body is pivotably coupled with the housing.

7. The surgical instrument of claim 6, wherein the projection is configured to pivot the locking body as the arm pivots toward the housing.

8. The surgical instrument of claim 7, wherein the projection defines a latch pocket.

9. The surgical instrument of claim 8, wherein the latch pocket is dimensioned to house a portion of the locking body while the latch assembly is in the latched configuration.

10. The surgical instrument of claim 9, wherein the locking body is biased to an upward position.

11. The surgical instrument of claim 1, wherein the arm is configured to transition the latch assembly between the latched configuration and the unlatched configuration.

12. The surgical instrument of claim 11, wherein the arm is configured to actuate toward the housing in order to transition the latch assembly between the latched configuration and the unlatched configuration.

13. The surgical instrument of claim 1, wherein the arm further comprises a thumb ring, wherein a portion of the latch assembly is coupled the thumb ring.

14. The surgical instrument of claim 1, further comprising an electrode activation assembly comprising a trigger, wherein the trigger is configured to activate the electrode assembly.

15. A surgical instrument comprising:
(a) an end effector, wherein the end effector comprises:
  (i) a first jaw,
  (ii) a second jaw pivotably coupled with the first jaw, wherein the second jaw is operable to move between an open position and a closed position,
  (iii) a knife configured to actuate between a pre-fired position and a fired position, and
  (iv) an electrode assembly configured to apply RF energy to tissue;
(b) a handle assembly, wherein the handle assembly comprises:
  (i) a housing associated with the first jaw, and
  (ii) an arm associated with the second jaw, wherein the arm is configured to pivot the second jaw between the open position and the closed position, wherein the arm is configured to pivot relative to the housing; and (c) a latching assembly comprising:
  (i) a locking body pivotably coupled with the housing, wherein the locking body comprises a lockout surface, and
  (ii) a camming body associated with the arm, wherein the camming body is configured to pivot the locking body relative to the housing and the arm in response to actuating the arm relative to the housing in order transition the latching assembly between an unlatched configuration and a latched configuration, wherein the latching assembly is configured to prevent the arm from pivoting the second jaw from the closed position to the open position in the latched configuration,
  wherein the locking surface of the locking body is configured to inhibit distal actuation of the knife while the latching assembly is in the unlatched configuration.

16. The surgical instrument of claim 15, wherein the locking body comprises a catch protrusion, wherein camming body defines a latch pocket dimensioned to house the catch protrusion in the latched configuration.

17. The surgical instrument of claim 15, wherein the locking body is biased to an upward position.

18. A surgical instrument comprising:
(a) an end effector, wherein the end effector comprises:
  (i) a first jaw,
  (ii) a second jaw pivotably coupled with the first jaw, wherein the second jaw is operable to move between an open position and a closed position,
  (iii) a knife configured to actuate between a pre-fired position and a fired position, and
  (iv) an electrode assembly configured to apply RF energy to tissue; and
(b) a handle assembly, wherein the handle assembly comprises:
  (i) a housing associated with the first jaw, and
  (ii) an arm associated with the second jaw, wherein the arm is configured to pivot the second jaw between the open position and the closed position, wherein the arm is configured to pivot relative to the housing between a first position, a second position, and a third position, wherein the second jaw is configured to be in the open position while the arm is in the first position, wherein the second jaw is configured to be in the closed position while the arm is in the second position and the third position; and
(c) a latching assembly configured to transition between an unlatched configuration and a latched configuration, wherein the latching assembly is configured to inhibit the arm from pivoting the second jaw from the closed position to the open position in the latched configuration, wherein the latching assembly is configured to transition between the latched configuration and the unlatched configuration in response to the arm actuating between the second position and the third position, wherein the latching assembly comprises a locking body configured to rotate relative to the housing and the arm as the latching assembly transitions between the latched configuration and the unlatched configuration, wherein the locking body is configured to inhibit distal translation of the knife in the unlatched configuration.

* * * * *